(12) United States Patent
Park

(10) Patent No.: US 10,576,219 B2
(45) Date of Patent: Mar. 3, 2020

(54) PEN NEEDLE PROVIDED WITH SAFETY PROTECTION SYSTEM

(71) Applicant: MEDEXEL CO., LTD., Gyeonggi-do (KR)

(72) Inventor: Wonguy Park, Gyeonggi-do (KR)

(73) Assignees: MEDEXEL CO., LTD., Gyeonggi-do (KR); WONGUY PARK, Gyeonggi-do (KR)

( * ) Notice: Subject to any disclaimer, the term of this patent is extended or adjusted under 35 U.S.C. 154(b) by 309 days.

(21) Appl. No.: 15/548,674

(22) PCT Filed: Jun. 30, 2016

(86) PCT No.: PCT/KR2016/007003
§ 371 (c)(1),
(2) Date: Aug. 3, 2017

(87) PCT Pub. No.: WO2017/065386
PCT Pub. Date: Apr. 20, 2017

(65) Prior Publication Data
US 2018/0028764 A1 Feb. 1, 2018

(30) Foreign Application Priority Data
Oct. 17, 2015 (KR) ........................ 10-2015-0145029

(51) Int. Cl.
*A61M 5/32* (2006.01)
*A61M 5/50* (2006.01)
*A61M 5/00* (2006.01)

(52) U.S. Cl.
CPC ........ *A61M 5/3293* (2013.01); *A61M 5/3202* (2013.01); *A61M 5/326* (2013.01);
(Continued)

(58) Field of Classification Search
CPC ...... A61M 5/32; A61M 5/3205; A61M 5/321; A61M 5/3245; A61M 2005/3268;
(Continued)

(56) References Cited

U.S. PATENT DOCUMENTS 6,015,397 A * 1/2000 Elson ................. A61M 5/3275
604/192
6,375,640 B1 * 4/2002 Teraoka ........... A61M 25/0625
604/162
(Continued)

FOREIGN PATENT DOCUMENTS

JP 2001-286562 10/2001 ............. A61M 5/32
JP 2011-512196 4/2011 ............. A61M 5/32
(Continued)

OTHER PUBLICATIONS

International Search Report from corresponding PCT Application No. PCT/KR2016/007003 dated Oct. 5, 2016 and its English translation.
(Continued)

*Primary Examiner* — Jason E Flick
(74) *Attorney, Agent, or Firm* — Harness, Dickey & Pierce, P.L.C.

(57) ABSTRACT

The present invention relates to a pen needle provided with a safety protection system, which utilizes a shuttlecock-shaped supporter blade of an elastic material to simplify the structure and reduce the number of parts to reduce the manufacturing process and size of the pen needle, thereby providing a less expensive, simpler and safer pen needle, in order to prevent the pen needle, which is a one-time consumable item to be inserted and fastened into a pen-type syringe in a screw-coupled manner, from being reused after a single use.

20 Claims, 25 Drawing Sheets

(52) U.S. Cl.
CPC ............... *A61M 5/50* (2013.01); *A61M 5/002* (2013.01); *A61M 2005/3247* (2013.01); *A61M 2005/3267* (2013.01)

(58) Field of Classification Search
CPC .. A61M 2005/3247; A61M 2005/3267; A61M 5/002; A61M 5/3202; A61M 5/326; A61M 5/3293; A61M 5/50
USPC ........................................................ 604/110
See application file for complete search history.

(56) References Cited

U.S. PATENT DOCUMENTS

| | | | |
|---|---|---|---|
| 2003/0060776 A1 | 3/2003 | Heiniger | |
| 2005/0171485 A1* | 8/2005 | Larsen | A61M 5/326 604/198 |
| 2007/0276338 A1 | 11/2007 | Shue et al. | 604/187 |
| 2012/0277685 A1 | 11/2012 | Limaye | 604/192 |
| 2017/0136183 A1* | 5/2017 | Helmer | A61M 5/2466 |

FOREIGN PATENT DOCUMENTS

| | | | |
|---|---|---|---|
| JP | 2012-500063 | 1/2012 | A61M 5/31 |
| JP | 2015-112489 | 6/2015 | A61M 5/32 |
| KR | 10-1994-0006609 | 4/1994 | A61M 5/32 |
| KR | 20-2000-0020090 | 11/2000 | A61M 5/178 |
| KR | 10-2001-0040365 | 5/2001 | A61M 5/178 |
| KR | 10-1589006 | 1/2016 | A61M 5/50 |

OTHER PUBLICATIONS

Office Action from corresponding Chinese Patent Application No. 201680013014.4, dated Oct. 30, 2019.

* cited by examiner

US 10,576,219 B2

PEN NEEDLE PROVIDED WITH SAFETY PROTECTION SYSTEM

CROSS-REFERENCE TO RELATED APPLICATIONS

This application is a national phase application of PCT Application No. PCT/KR2016/007003, filed on 30 Jun. 2016, which claims priority to Korean Patent Application No. 10-2015-0145029, filed on 17 Oct. 2015. The entire disclosures of the applications identified in this paragraph is incorporated herein by reference.

TECHNICAL FIELD

The present disclosure relates to a pen needle provided with safety protection system capable of preventing the pen needle, which is a one-time consumable and is inserted into and coupled to a pen-type syringe in a screw-coupling manner, from being reused after a single use, and more particularly, to a pen needle provided with a safety protection system, which utilizes a shuttlecock-shaped supporter blade of an elastic material to simplify the structure and reduce the number of parts to reduce the manufacturing process and size of the pen needle, thereby providing a less expensive, simpler and safer pen needle.

BACKGROUND ART

A pen-type syringe is easily carried and used when administration of a dose of medication is regularly needed, such as insulin administration and the like.

Due to a risk, such as infection and the like, the pen-type syringe is used by mounting hub equipped with a disposable needle whenever used. The needle is mounted on the center of the hub, and, in the present disclosure, the hub on which the needle is mounted is referred to as a pen needle.

As shown in FIG. 1, a commercially available needle set is generally configured to include a hub 400 on which a needle N is mounted, a tip cap 250, a large cap 500, and a sterilized sheet finishing material 290. In the present disclosure, a commercially available needle, which is configured with a hub having a needle, a tip cap, a large cap, and a sterilized sheet finishing material, is referred to as a needle set.

In a needle set, a tip cap covers a needle disposed at the center of a hub, a large cap is mounted over the tip cap, and a sterilized sheet finishing material is attached to a lower surface of the hub before the needle set is used. When the needle set is used, the sterilized sheet finishing material is removed, the hub having the needle that is covered with the large cap and the tip cap is mounted on a pen-type syringe, and then the large cap and tip cap are removed to perform injection. Generally, after using the needle, the tip cap or the large cap is remounted over the needle and then the hub is separated from the syringe to be discarded.

After using the hub on which the needle is mounted, a case in which, when the pen-type syringe and the hub are separated from each other, a user may be stuck with the needle while remounting the tip cap on the needle, or a case in which, when the separation between the pen-type syringe and the hub is performed without covering the tip cap on the needle, the user may be carelessly stuck with the needle while revolving the hub to perform a screw release, which frequently occurs.

Even after separating the hub having the needle which is used once and contaminated, there is an inconvenience in safely discarding medical waste, and there is also a possibility that the hub having the needle, which is a one-time consumable, may be reused.

Conventionally, a safety protection system separated from a pen needle has been widely developed to prevent reuse of a disposable needle which is used once and then discarded, but there is a burden on a user to purchase such a safety protection system at an additional cost and there is an inconvenience in that the user separately manages such a safety protection system.

That is, a conventional pen needle coupled to a syringe pen and disposably used has a form in which a needle protrudes from a hub toward the outside to be directly exposed to a user, and thus concerns such as needle sticks and the like exist, and the conventional pen needle that is a one-time consumable may be reused many times, and thus a risk such as secondary infection and the like exist, and thus a safety pen needle provided with a safety function and a structure for preventing reuse is necessarily needed for securing safety of a user in connection with health and safety issues.

Consequently, a safety protection system for a pen needle is required to block a repetitive reuse of a pen needle including a hub coupled to a pen-type syringe and having a needle (that is, an injection needle) which is provided at the center of the hub and is used as a one-time consumable, and to prevent pain and infection due to needle sticks.

Specifically, a safety protection system for a pen needle which is inexpensive, has a small size, is simple and easily carried, and is safer in use is required.

The present disclosure proposes a safety protection system for a pen needle which utilizes a shuttlecock-shaped supporter blade of an elastic material to simplify the structure and reduce the number of parts to reduce the manufacturing process and size of the pen needle.

Generally, as shown in FIG. 2, a syringe main body 605 is manufactured by plastic injection, is capable of assuring an antimicrobial property, is configured with a structure capable of administrating a dosage of a certain amount of an injection medication several to tens of times, and is provided with a scale part having a transparent window on which a scale is provided and configured to indicate a remaining amount of the injection medication, a pressing plate for administrating injection medication is provided at a lower end of the syringe main body 605, and a hub mounting part 54 for mounting a hub 400 having a needle N is provided at an upper end of the syringe main body 605. A syringe screw part 601 having a helically-shaped screw thread and serving as a male screw is provided at the hub mounting part 54 and is coupled to a hub screw part 407 that is provided inside the hub 400 so that the hub 400 having the needle N is engaged with an upper end portion of the syringe main body 605.

That is, a pen needle, which collectively refers to a hub having a needle at the center of the hub, is mounted on the syringe screw part 601 at the upper end of the syringe main body 605. Generally, a pen-type syringe is configured to administer a certain amount of a medication to a human body by a pressing pressure of a user, and is able to be disposably used by a pen needle being replaced whenever the pen needle is used due to a risk such as infection and the like.

FIG. 3a is a perspective view illustrating a needle fixing body 404 in a hub, and FIG. 3b is a perspective view illustrating the hub screw part 407 in the hub.

The hub 400 is provided with a needle fixing body 404 disposed at the center of an upper end 430 of a hub lower body 440, and a needle fixing body protrusion 421 disposed at an outer side of the needle fixing body 404, and the needle fixing body protrusion 421 and the needle fixing body 404 are inserted into a hub corresponding part 251 of the tip cap 250. The hub lower body 440 and the needle fixing body 404 are stepped. A needle insertion through-hole 405 is provided at the center of an upper end of the needle fixing body 404 to enable the needle N to be inserted thereinto.

A hub screw part 407 having a helically-shaped screw thread and serving as a female screw is provided at an inner side of the hub lower body 440 so that the hub lower body 440 is coupled to the syringe screw part 601. In the hub 400 having the needle N, the needle fixing body 404 and the needle N are covered with the tip cap 250. The large cap 500 is mounted over the hub 400 on which the tip cap 250 is mounted as described above.

A plurality of hub lower body protrusions 408, which are each formed in a bar shape, and a plurality of hub body recesses 442, which are each formed between every two of the plurality of hub lower body protrusions 408, are provided at an external wall of a hub lower body 440. The plurality of hub lower body protrusions 408 are each inserted into inner side recesses (not shown) provided at a lower portion of an inner side of the large cap 500, and thus the hub 400 and the large cap 500 are engaged.

The needle N is inserted into the needle insertion through-hole 405 provided at a central portion of the hub 400 to pass therethrough.

As a related art, Japanese Patent Application Publication Nos. 2012-500063 and 2011-512196 disclose a safe pen needle assembly. Such a safe pen needle assembly has a complicated structure, and thus a unit price thereof may be relatively high.

As another related art, Japanese Patent Application Publication No. 2001-286562 discloses "Safety Treatment Cap Assembly for Medical Use" and Japanese Patent Application Publication No. 2015-112489 discloses "Adaptive Safety Pen Needle Assembly," and each of these assemblies also has a complicated structure so that assembling is not easy and a unit price thereof may be relatively high.

As still another related art, U.S. Patent Application Publication No. 2012-0277685 discloses that a shield into which a needle is inserted is formed to be a cylindrical shape, and thus, in some cases, when the needle (that is, an apex end part) is moved to be used, the needle may be damaged due to a collision with a wall of the shield.

Like the above-mentioned related art, the pen needle provided with a newly attempted safety function and a safety function restricted for the purpose of one-time use inevitably has a complicated structure due to an increase of the number of components configured to implement reuse prevention and safety functions in comparison with a typical pen needle, a manufacturing process thereof is also inevitably complicated, and further a size of an exterior appearance of the pen needle is greater than that of an exterior appearance of the typical pen needle in addition to manufacturing costs thereof being increased, so that a psychological burden on a user is finally increased with respect to the size of the pen needle, which is a one-time consumable, when the user engages the pen needle with a pen-type syringe to administer an injection medication to him or herself, and an economic burden on the user due to an increased purchase cost is increased.

However, the present disclosure provides a pen needle provided with a safety protection system, which utilizes a shuttlecock-shaped supporter blade of an elastic material to simplify the structure and reduce the number of parts to reduce the manufacturing process and size of the pen needle, thereby providing a less expensive, simpler and safer pen needle.

DISCLOSURE

Technical Problem

Therefore, an objective of the present disclosure is to provide a pen needle provided with a safety protection system capable of preventing reuse of a pen needle which is a one-time consumable and is inserted into and coupled to a pen-type syringe in a screw-coupling manner, which utilizes a shuttlecock-shaped supporter blade of an elastic material to simplify the structure and reduce the number of parts to reduce the manufacturing process and size of the pen needle, thereby providing a less expensive, simpler and safer pen needle.

Another objective of the present disclosure is to provide a pen needle provided with a safety protection system, which is manufactured with a simple principle and easily used compared to a conventional pen needle provided with safety functions, has a simplified structure and simplified functions to reduce frequency of a minor failure, and is capable of dramatically reducing the number of components to decrease an entire size such that a psychological burden on a user is decreased with respect to the size of the pen needle when the user administers an injection medication, and manufacturing costs are decreased by the reduction of the number of components to reduce an economic burden on the user.

Technical Solution

To resolve the above-described problems, in accordance with the present disclosure, a pen needle configured such that, when an injection medication administration push button is pressed and a needle protrudes outside a small cap (first cap) through a small cap upper surface (first cap upper surface) through-hole and then the injection medication administration push button is released, the needle is inserted into the small cap through the small cap upper surface through-hole to be prevented from protruding outside the small cap through the small cap upper surface through-hole is provided, the pen needle including a wing-type support unit provided with a needle fixing body insertion tube having a cylindrical shape, and having a plurality of wing-type support wings disposed along a rim of the needle fixing body insertion tube; the small cap having a ring-shaped small cap upper surface connected to and installed at a small cap cylindrical wall body (first cap cylindrical wall body), and configured to enable the wing-type support unit to be inserted into the small cap; and a hub provided with a needle fixing body into which the needle is inserted at a center of the hub, and configured to enable the needle fixing body to be moved according to whether the injection medication administration push button is pressed, wherein the needle fixing body is inserted into the needle fixing body insertion tube.

The pen needle may further include a spring mounted around the needle fixing body.

The small cap may be provided below the small cap cylindrical wall body, wherein the small cap may further be provided with a small cap supporter having a wing-type support unit insertion through-hole at a center of the small cap, and the spring may be located below the small cap supporter.

A wing-type support unit blocking bump may be provided at a bottom surface of the small cap supporter to block unfolding of the plurality of wing-type support wings when the wing-type support unit is moved below the small cap supporter.

A wing-type support unit recess may be provided at a lower portion of the needle fixing body insertion tube, and a needle fixing body bump may be provided at a lower portion of the needle fixing body.

The wing-type support unit recess may be provided at the lower portion of the needle fixing body insertion tube, and a wing-type support unit fixer having a hook shape may be provided at an upper surface of a hub lower body around the needle fixing body.

When the wing-type support unit is moved below the small cap supporter, the wing-type support unit recess and the needle fixing body bump may be engaged or the wing-type support unit recess and the wing-type support unit fixer may be engaged.

In the pen needle, a medium cap (second cap) may be provided at an outer side of the small cap cylindrical wall body (second cap cylindrical wall body), mounted over the hub lower body, and have a ring-shaped medium cap upper surface (second cap upper surface) that is connected to and installed at a medium cap cylindrical wall body.

The hub may further be provided with a medium cap fixer (second cap fixer) having a fence shape at an upper surface rim of the hub lower body.

A medium cap fixing recess (second cap fixing recess) may be provided at an outer side of the medium cap fixer of the hub, a medium cap bump (second cap bump) may be provided at a lower portion of an inner side of the medium cap, and the medium cap fixing recess and the medium cap bump may be engaged.

A medium cap fixing bump may be provided at an outer side of the medium cap fixer of the hub, a medium cap body recess (second cap body recess) may be provided at a lower portion of the inner side of the medium cap, and the medium cap fixing bump and the medium cap body recess may be engaged.

Also, in accordance with the present disclosure, a pen needle configured such that, when an injection medication administration push button is pressed and a needle protrudes outside a small cap through a small cap upper surface through-hole and then the injection medication administration push button is released, the needle is inserted into the small cap through the small cap upper surface through-hole to be prevented from protruding outside the small cap through the small cap upper surface through-hole is provided, the pen needle including the small cap having a ring-shaped small cap upper surface connected to and installed at a small cap cylindrical wall body; a wing-type support unit provided with a needle fixing body insertion tube having a cylindrical shape, having a plurality of wing-type support wings disposed along a rim of the needle fixing body insertion tube, inserted inside the small cap cylindrical wall body, and moved according to whether the injection medication administration push button is pressed; and a hub provided with a needle fixing body into which the needle is inserted at a center of the hub, wherein the needle fixing body is inserted into the needle fixing body insertion tube.

The pen needle may further include a spring mounted around the needle fixing body, the small cap may be provided below the small cap cylindrical wall body and may further be provided with a small cap supporter having a wing-type support unit insertion through-hole at a center of the small cap, the spring may be located below the small cap supporter, the small cap may be provided below the small cap cylindrical wall body and may be further provided with a small cap supporter having a wing-type support unit insertion through-hole at a center of the small cap, and the spring may be located below the small cap supporter.

The pen needle may further include a medium cap provided at an outer side of the small cap cylindrical wall body, mounted at an outer side of the hub lower body, and having a ring-shaped medium cap upper surface that is connected to and installed at a medium cap cylindrical wall body.

A hub fixing bump may be provided at an inner side of the medium cap, and a medium cap screw part is provided below the hub fixing bump.

The hub may be provided with a plurality of wing-type support unit fixers having a hook shape at an upper surface of the hub lower body around the needle fixing body, and a screw part is provided at a lateral surface of the outer side of the hub lower body.

A plurality of medium cap external protrusions having a rod shape may be provided at an outer side wall of the medium cap.

The small cap may be configured such that a small cap cylindrical wall body upper part of the small cap cylindrical wall body is formed to have a radius that decreases toward an upper end of the small cap.

The small cap may be configured such that the wing-type support unit insertion through-hole is located to be lower than an upper surface of a small cap supporting plate wing-shaped protrusion, which is a small cap supporter located at the outer side of the small cap cylindrical wall body.

Advantageous Effects

In accordance with the present disclosure, a pen needle provided with a safety protection system is capable of preventing reuse of a pen needle, which is a one-time consumable and is inserted into and coupled to a pen-type syringe in a screw-coupling manner, by a user after the pen needle is used once by reducing the number of components using a shuttlecock-shaped supporter blade made of an elastic material to simplify a structure and reduce a size of a pen needle so that the pen needle is less expensive, simpler, and more secure, and a manufacturing process thereof.

Also, in accordance with the present disclosure, the pen needle provided with a safety protection system is manufactured with a simple principle and is easily used compared to a conventional pen needle provided with safety functions, has a simplified structure and simplified functions to reduce the frequency of a minor failure, and is capable of dramatically reducing the number of components to decrease an entire size such that a psychological burden on a user is decreased with respect to the size of the pen needle when the user administers an injection medication, and manufacturing costs are decreased by the reduction of the number of components to reduce an economic burden on the user.

In other words, the present disclosure employs a safety protection system for a pen needle to primarily prevent reuse of the pen needle, which is engaged with a pen-type syringe that is disposably used for various therapeutic purposes and multiple purposes, after the pen needle is used once, and prevent secondary infection by the needle piercing a user due to carelessness.

A small cap, a medium cap, a shuttlecock-shaped supporter blade, and a spring are assembled with a hub configuring the pen needle of the present disclosure, and thus the pen needle is configured with a very simple and easy structure so that an economic tradeoff between utility and manufacturing costs may be reduced. Also, in accordance with the present disclosure, a spring is embedded and located inside a medium cap, which is a space separated from a needle, such that there is no concern that the needle will come into direct contact with the spring. Specifically, in accordance with the present disclosure, the number of components configuring the safety protection system for a needle is fewer, and thus an entire size of the pen needle is small and a minor failure hardly occurs such that there is an effect in which a probability of injection failure due to malfunction may be dramatically reduced. Further, in accordance with the present disclosure, the pen needle is configured to have the form of an assembly to be able to be miniaturized in size so that there is an effect in that a psychological burden on a user with respect to a size of the pen needle when the user administers an injection medication to him or herself is reduced.

MODES OF THE INVENTION

Hereinafter, a pen needle provided with a safety protection system of the present disclosure will be described in detail with reference to the accompanying drawings.

Figure 1:
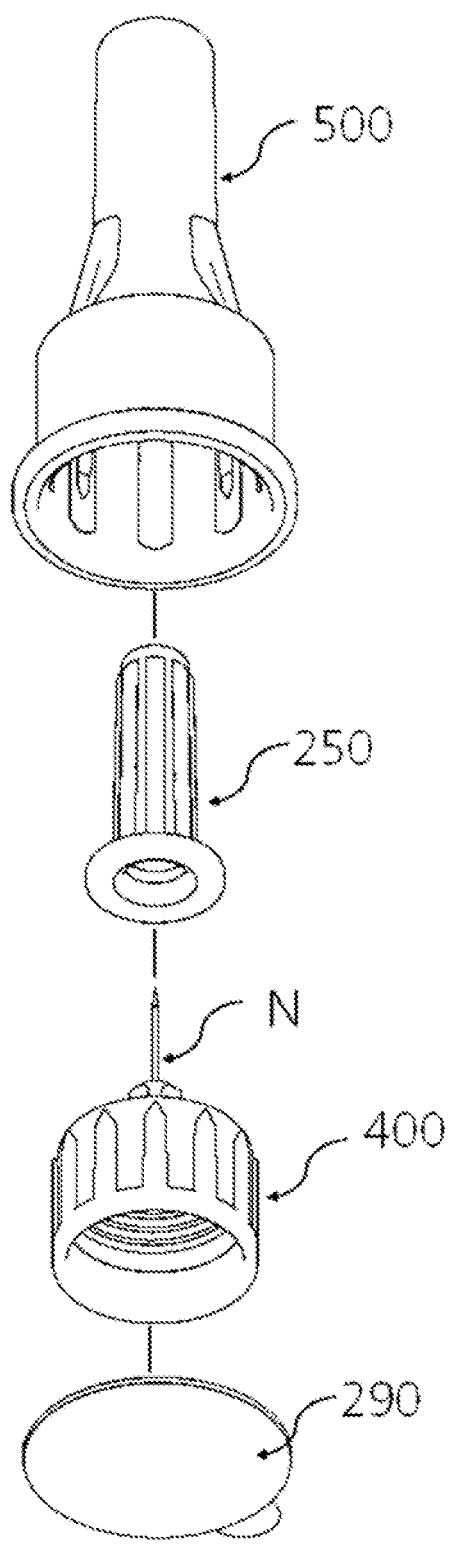
FIG. 1 is an exploded perspective view of a needle set.
Figure 2:
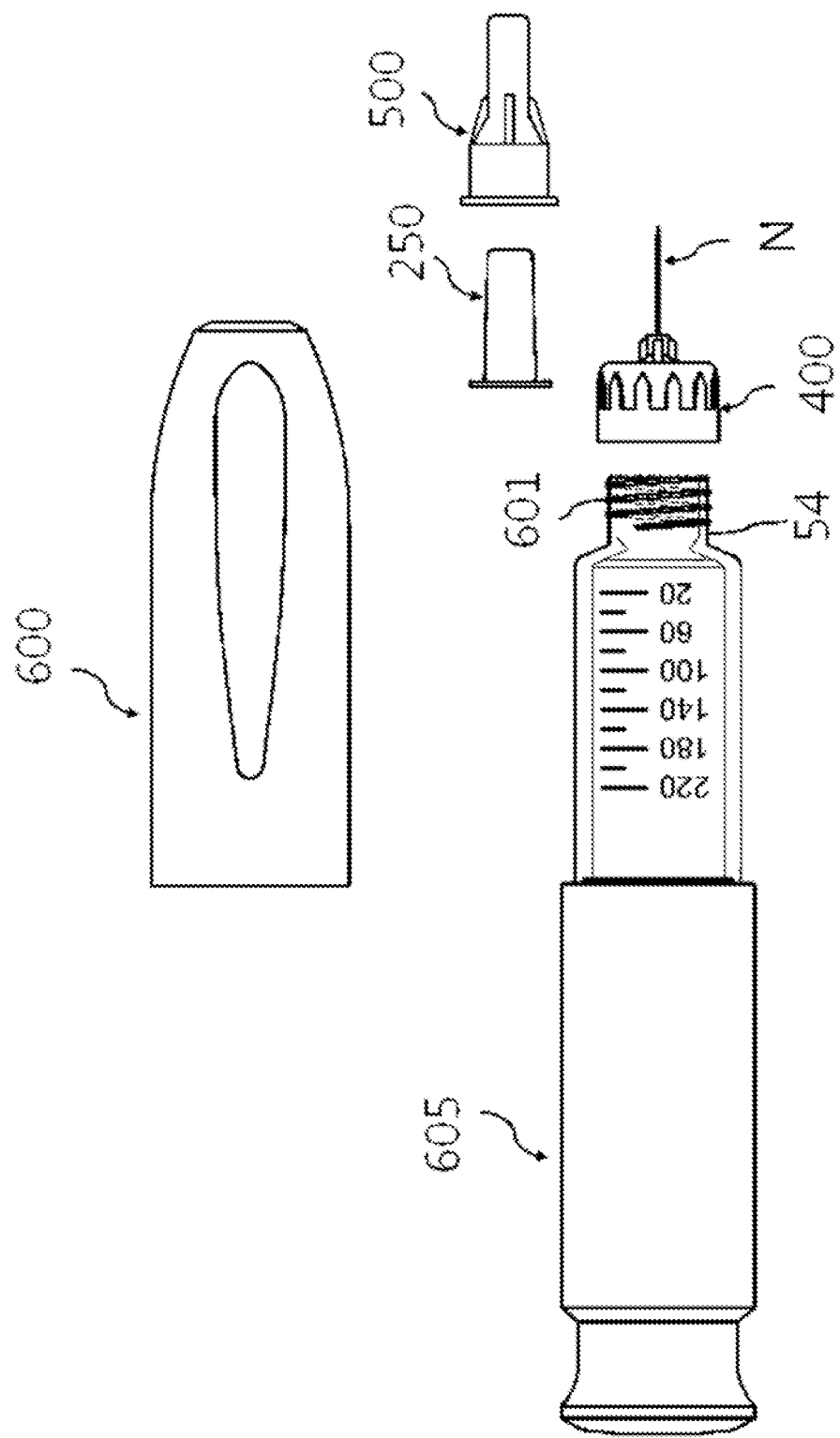
FIG. 2 is a diagram for describing a configuration of one example of a pen-type syringe set.
Figure 3:
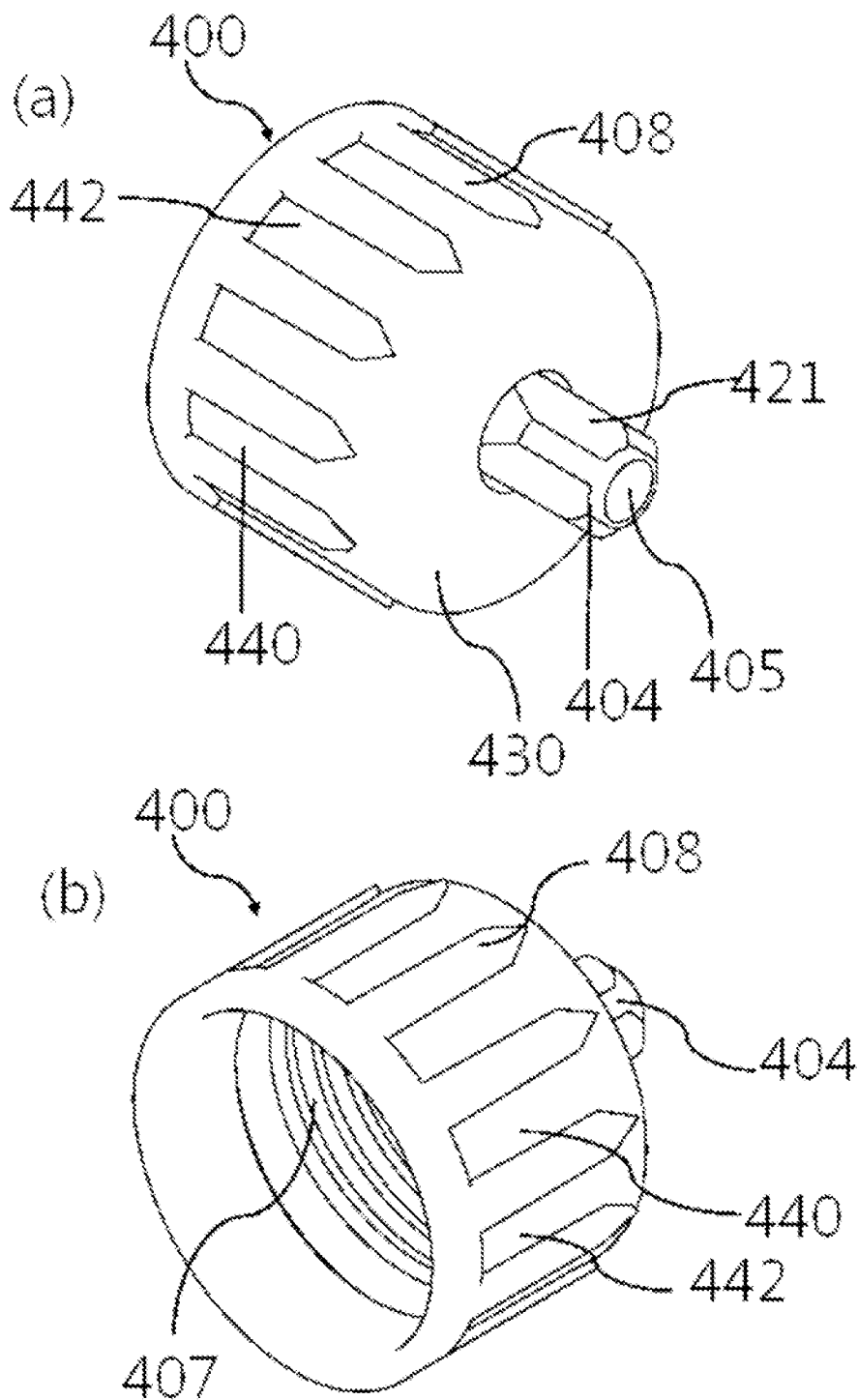
FIG. 3 is a perspective view of a hub of FIG. 2.
Figure 4:
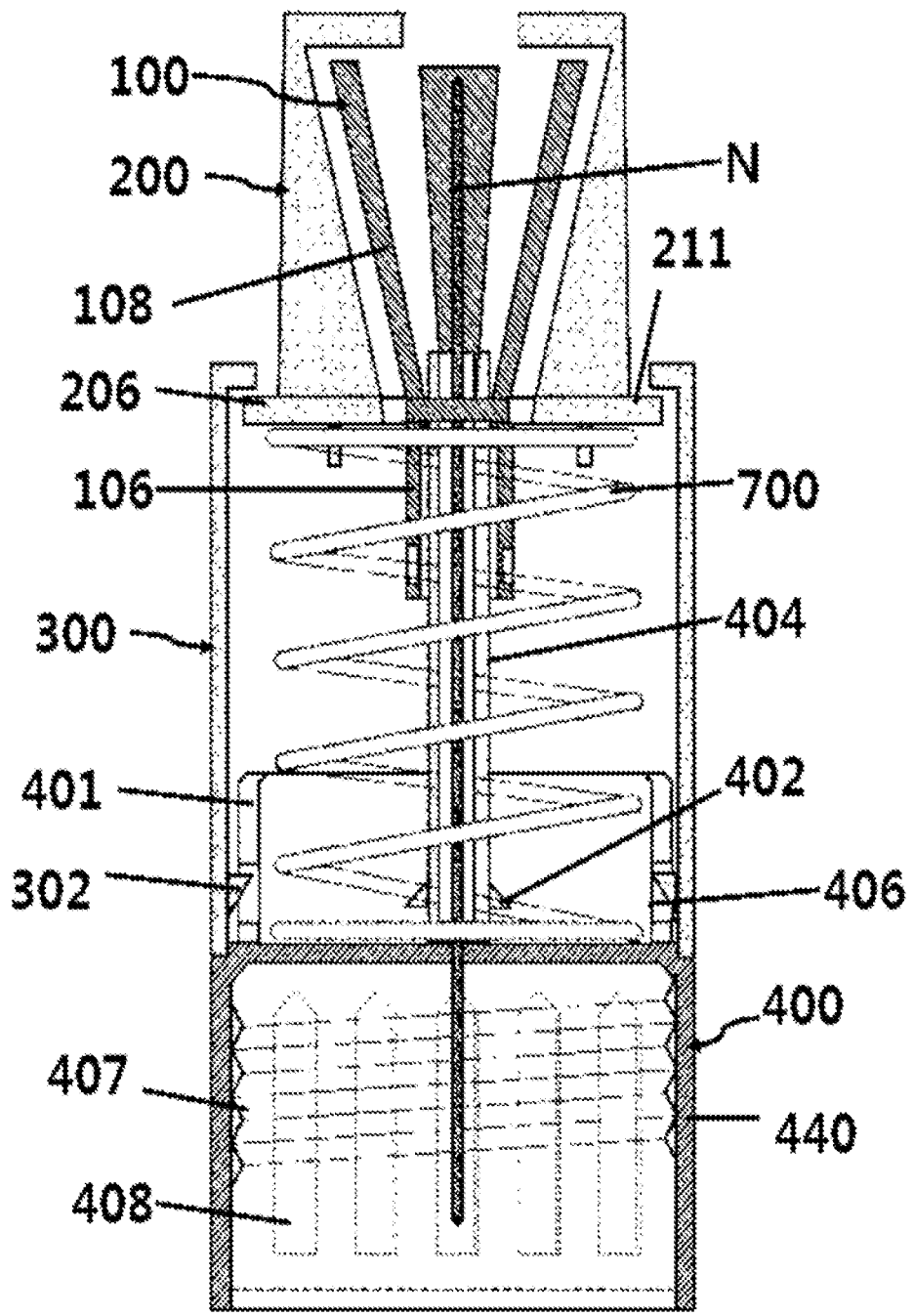
FIG. 4 is a diagram for schematically describing a configuration of a pen needle provided with a safety protection system according to a first embodiment of the present disclosure.

FIG. 4 is a diagram for schematically describing a configuration of a pen needle provided with a safety protection system according to a first embodiment of the present disclosure.

A hub 400 is configured with a needle fixing body 404 having a long tube shape and provided at the center of an upper end of a hub lower body 440, and a medium cap fixer 401 having a rounded fence-like shape and provided at an upper surface rim of the hub lower body 440.

A spring 700 is mounted at an outer side of the needle fixing body 404, and a needle fixing body bump 402 is provided at a lower portion of the outer side of the needle fixing body 404. Here, the needle fixing body bump 402 may be a ring-shaped bump. A small cap 200 is mounted over the spring 700.

The medium cap fixer 401 is provided with a medium cap fixing recess 406 in the form of a shape of a through-hole or recess, a medium cap 300 is mounted at an outer side of the medium cap fixer 401, and the medium cap fixing recess 406 is coupled to a medium cap bump 302 provided at a lower portion of an inner side of the medium cap 300 to engage the hub 400 with the medium cap 300. A height of the medium cap fixer 401 is lower than that of each of the medium cap 300 and the needle fixing body 404.

The small cap 200 is provided with a small cap supporting plate (or a small cap supporter) 206 having a wing-type support unit insertion through-hole 204, a small cap cylindrical wall body 210 is provided on the small cap supporting plate 206, and a small cap upper surface 202 having a small cap upper surface through-hole 203 is connected to and installed on the small cap cylindrical wall body 210. The small cap cylindrical wall body 210 is configured to have a thickness that increases toward a lower portion of the small cap cylindrical wall body 210, and a space formed by the small cap cylindrical wall body 210 is a wing-type support unit accommodation part 201. Consequently, the wing-type support unit accommodation part 201 is also configured to have a radius that decreases toward a lower portion of the wing-type support unit accommodation part 201.

A wing-type support unit 100 having a shuttlecock shape is inserted into the wing-type support unit accommodation part 201 to vertically move therethrough, and is configured such that only a needle N is able to protrude through the small cap upper surface through-hole 203 while the wing-type support unit 100 is not able to protrude through the small cap upper surface through-hole 203.

When using the needle N, the wing-type support unit 100 is located below the needle fixing body bump 402 of the needle fixing body 404 due to stretching of the spring 700 such that a wing-type support unit lower bump 104, which is a bump of a lower portion of an inner side of the wing-type support unit 100, and the needle fixing body bump 402 are coupled, and, after injection is completed, that is, after a user releases a pressing plate of a syringe, the spring 700 is restored so that the needle N is located in the wing-type support unit accommodation part 201 while the wing-type support unit 100 is located below the small cap supporting plate 206. In some cases, the needle fixing body 404 may be provided with a protrusion or bump (not shown), and the protrusion or bump (not shown) may be coupled to a wing-type support unit recess 109.

The wing-type support unit 100 is mounted over the needle fixing body 404 into which the needle N is inserted, and is then inserted into the wing-type support unit insertion through-hole 204.

The small cap supporting plate 206 is provided with the wing-type support unit insertion through-hole 204 to form a ring-shaped circular plate, and is configured to have a radius that is greater than that of the small cap cylindrical wall body 210 to provide a small cap supporting plate wing-shaped protrusion 211, which is a step formed by the small cap cylindrical wall body 210 and the small cap supporting plate 206. The small cap supporting plate wing-shaped protrusion 211 is configured not to deviate from a medium cap upper surface bump 301.

Figure 5:
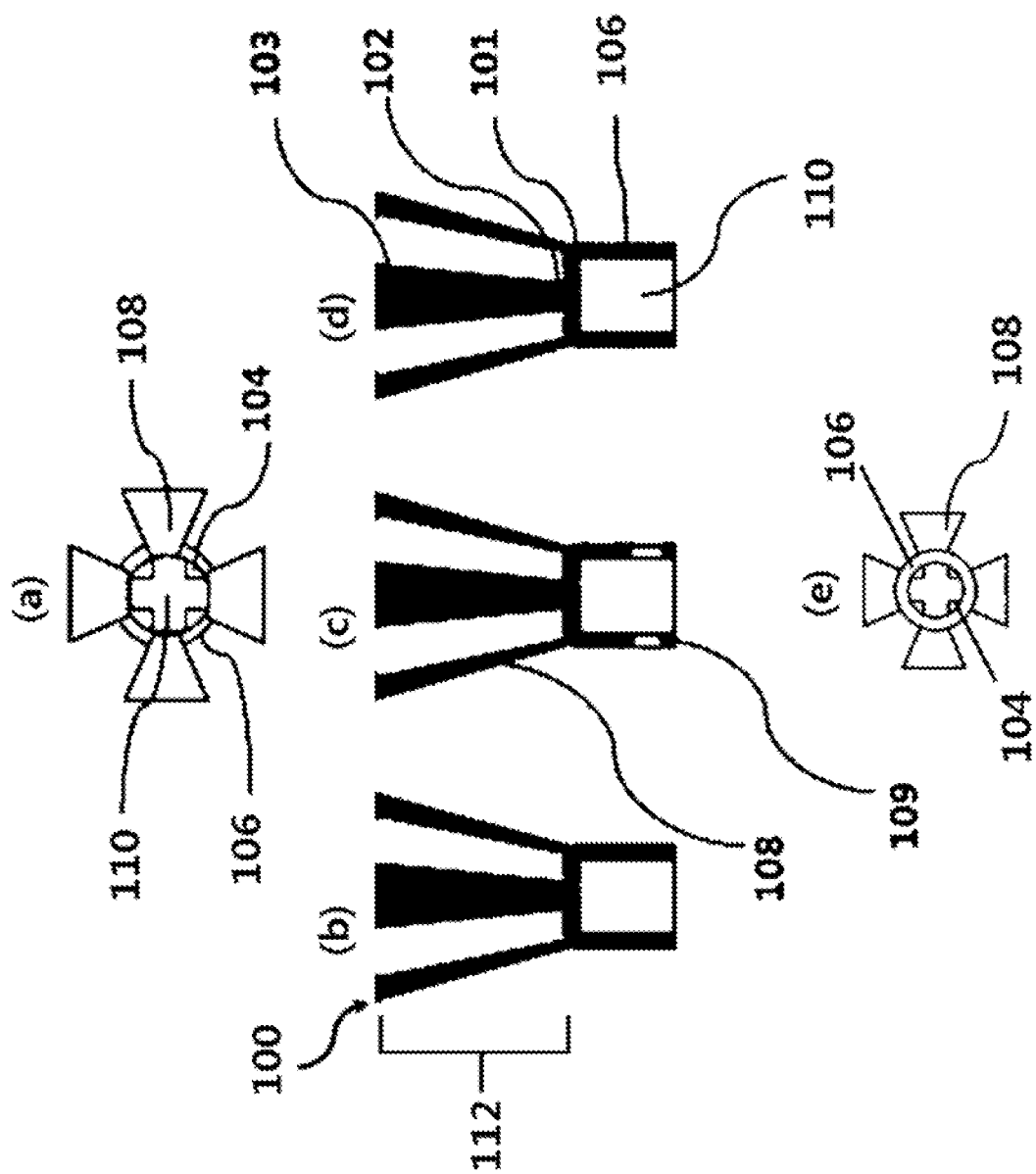
FIG. 5 is a cross sectional development view of a wing-type support unit of FIG. 4.

FIG. 5 is a cross sectional development view of the wing-type support unit of FIG. 4.

FIG. 5a is a diagram illustrating the wing-type support unit 100 when viewed from a top side thereof, FIG. 5b is a diagram illustrating the wing-type support unit 100 when viewed from a left side thereof, FIG. 5c is a diagram illustrating the wing-type support unit 100 when viewed from a front side thereof, FIG. 5d is a diagram illustrating the wing-type support unit 100 when viewed from a right side thereof, and FIG. 5e is a diagram illustrating the wing-type support unit 100 when viewed from a bottom side thereof.

The wing-type support unit 100 is a means for controlling the needle N to protrude and vertically move and for preventing reuse of the needle N.

A circular opening 110 is vertically provided at a central portion of the wing-type support unit 100, and the wing-type support unit 100 is made of an elastic plastic material or a metal material and has a form that is entirely similar to a shuttlecock in shape.

A needle fixing body insertion tube 106 is formed at a lower portion of the wing-type support unit 100, and a plurality of wing-type support unit wings 108 are provided at an upper portion of the wing-type support unit 100, that is, are connected to and installed at an upper end of the needle fixing body insertion tube 106.

Each of the plurality of wing-type support unit wings 108 is configured to have an inverted trapezoidal form, that is, to have a supporter wing in which a transverse length (that is, a width) thereof increases from a wing-type support unit lower wing 102 toward a wing-type support unit upper wing 103.

The wing-type support unit 100 is configured such that the plurality of wing-type support unit wings 108 having the inverted trapezoidal form are connected and installed along an upper end rim 101 of the cylindrical needle fixing body insertion tube 106, and a cross section of a wing-type support unit wing part 112 configured with the plurality of wing-type support unit wings 108 increases in an upward direction.

A portion of the needle fixing body 404 into which the needle N is inserted is inserted into the opening 110 of the needle fixing body insertion tube 106 to be located below the small cap upper surface 202. The upper portion of the wing-type support unit 100 is configured to be inserted into the wing-type support unit accommodation part 201 of the small cap 200 to vertically move in the wing-type support unit accommodation part 201 but not to protrude through the small cap upper surface through-hole 203.

When the small cap upper surface 202 comes into contact with skin and a pressing plate of a syringe body is pressed, the wing-type support unit lower bump 104, which is a bump of a lower portion of an inner side of the needle fixing body insertion tube 106, is coupled to the needle fixing body bump 402 which is located at the lower portion of the needle fixing body 404. The wing-type support unit lower bump 104 may be configured with a triangular protrusion.

In some cases, the needle fixing body bump 402 of the needle fixing body 404 may be configured with a partially protruding protrusion or bump instead of a ring-shaped bump, and the protrusion or bump (not shown) may be coupled to the wing-type support unit recess 109.

In other words, when the small cap 200 is moved downward inside the medium cap 300 due to a pressing pressure generated by contact between the small cap 200 and the skin of a user, the same pressing pressure is delivered to the wing-type support unit upper wing 103 in contact with the small cap upper surface 202 so that the wing-type support unit 100 accommodated inside the small cap 200 is also moved downward with the small cap 200 inside the medium cap 300. In this case, the needle N protrudes from an upper end of the small cap 200 to the outside thereof by a length corresponding to the downward movement of the small cap 200 inside the medium cap 300, and pierces the skin of the user by the length of the needle which protrudes outside so that the user may administer an injection medication to him or herself.

At this point, the protrusion or bump (not shown) of the needle fixing body 404 is inserted into a supporting rod and a wing-type support unit recess 109 so that the wing-type support unit 100 moved downward with the small cap 200 is fixed to and engaged with the needle fixing body 404, and, after the user administers the injection medication to him or herself, the small cap 200 is moved upward inside the medium cap 300 due to an elastic restoring force of the spring to return to an original position thereof while the wing-type support unit 100 is not moved upward with the small cap 200, and the wing-type support unit upper wing 103 supports an inner side surface of a wing-type support unit blocking bump 205 formed at a bottom of a lower portion of the small cap 200 that is completely moved upward such that the small cap 200 that moved downward once is prevented from being moved downward again to prevent reuse of the needle N.

Figure 6:
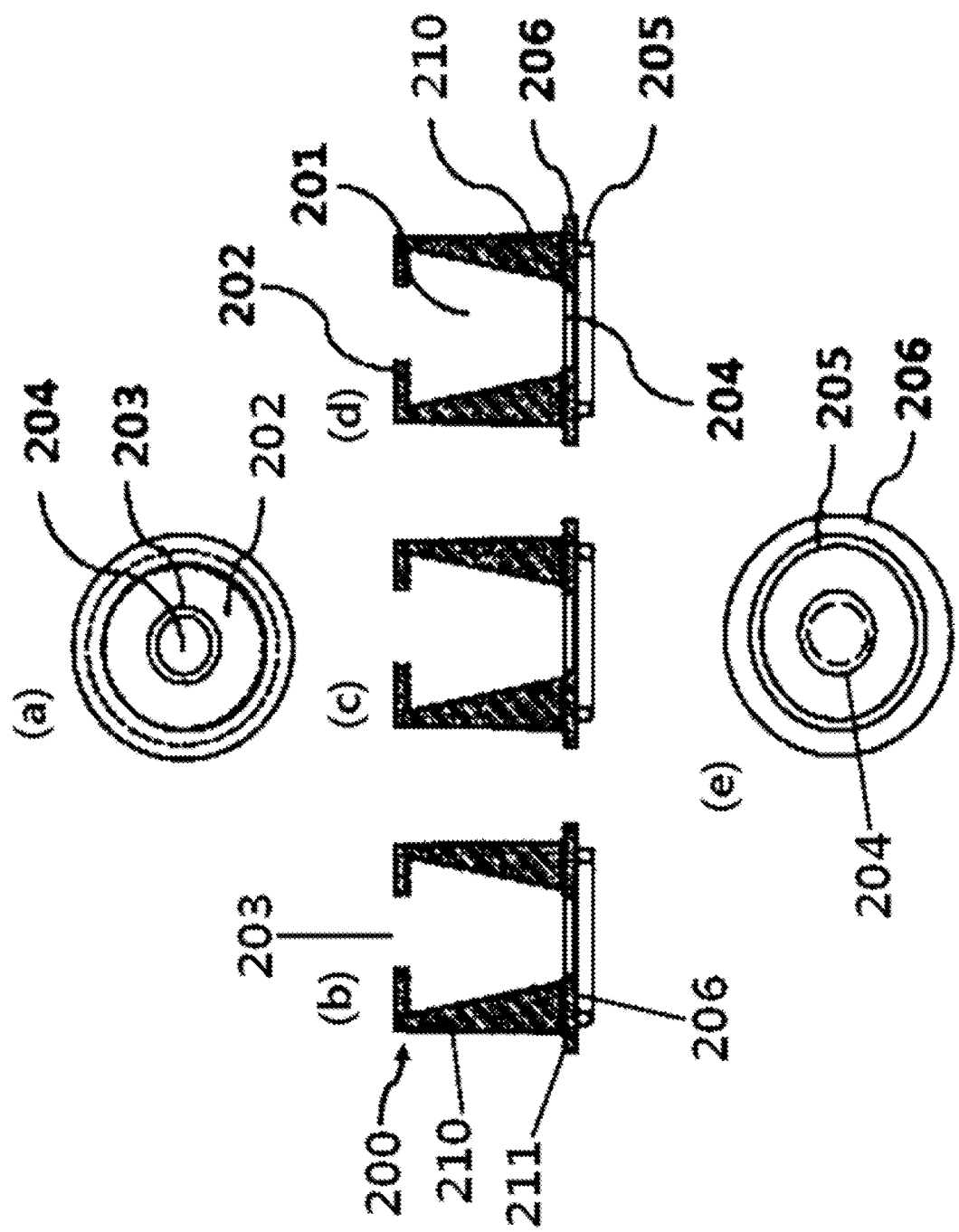
FIG. 6 is a cross sectional development view of a small cap of FIG. 4.

FIG. 6 is a cross sectional development view of the small cap of FIG. 4.

FIG. 6a is a diagram illustrating the small cap 200 when viewed from a top side thereof, FIGS. 6b, 6c, and 6d are diagrams each illustrating the small cap 200 when viewed from a left side, a front side, and a right side thereof, and FIG. 6e is a diagram illustrating the small cap 200 when viewed from a bottom side thereof. ii The small cap 200 is a means for accommodating the wing-type support unit 100 inside the wing-type support unit accommodation part 201 to restrict a movement of the wing-type support unit 100.

The small cap 200 accommodates the wing-type support unit 100 therein, is moved downward inside the medium cap 300 due to a pressing pressure generated by direct contact between the small cap 200 and the skin when the user administers the injection medication, and, after the injection medication is administered by the user, is moved upward again inside the medium cap 300 due to the elastic restoring force of the spring.

The small cap 200 is configured with the small cap supporting plate 206, the small cap cylindrical wall body 210, and the small cap upper surface 202.

The small cap supporting plate 206 is provided with the wing-type support unit insertion through-hole 204 to form a ring-shaped circular plate, and is configured to have a radius that is greater than that of the small cap cylindrical wall body 210 to provide the small cap supporting plate wing-shaped protrusion 211, which is an outer side rim of the small cap supporting plate 206.

The small cap cylindrical wall body 210 is a cylindrical wall body mounted on the small cap supporting plate 206 and is configured to have a thickness that increases toward the lower portion of the small cap cylindrical wall body 210, and the wing-type support unit accommodation part 201 formed by the small cap cylindrical wall body 210 is also configured to have a radius that decreases toward the lower portion of the wing-type support unit accommodation part 201.

The small cap upper surface 202 is connected to and installed at an upper portion of the small cap cylindrical wall body 210, and is provided with the small cap upper surface through-hole 203 at a central portion of the small cap upper surface 202. The small cap upper surface 202 serves as a bump (or a protrusion) that blocks protrusion of the wing-type support unit 100 that is inserted into the wing-type support unit accommodation part 201. That is, the small cap upper surface 202 may be a deviation prevention bump of the wing-type support unit 100.

The small cap upper surface through-hole 203 is larger than the wing-type support unit insertion through-hole 204.

In other words, the small cap supporting plate 206 having the small cap supporting plate wing-shaped protrusion 211, which is a circular band-shaped protrusion, is provided at an outer side of the lower portion of the cylindrical small cap 200 that is vertically circularly open, and is supported by an upper end of a wall surface of the medium cap 300 when the small cap 200 is vertically reciprocally moved in a spring accommodation part 303 inside the medium cap 300 due to a pressing pressure generated by the user and applied to the small cap 200 and the elastic force of the spring such that the small cap 200 is able to perform a vertical reciprocal movement in a balanced state, that is, a stable state.

Above all, the small cap supporting plate 206, that is, the small cap supporting plate wing-shaped protrusion 211, is hooked to a medium cap upper surface bump 301 provided at an upper end of the medium cap 300 such that deviation of the small cap 200, which is vertically supported by the elasticity of the spring 700 inside the medium cap 300, to the outside of the medium cap 300 is prevented.

The wing-type support unit blocking bump 205 is provided at a bottom surface of the small cap 200, has a radius that is even smaller than a diameter of the small cap supporting plate 206 and an inner diameter of the spring 700, and blocks the plurality of wing-type support unit wings 108 from unfolding when the plurality of wing-type support unit wings 108 are located below the small cap supporting plate 206. That is, in the case of a state in which the plurality of wing-type support wings unit 108 vertically support the small cap 200 inside the medium cap 300 after the user uses the pen needle once, the wing-type support unit blocking bump 205 serves to block the wing-type support unit upper wing 103 from unfolding and deviating from a pressing force applied to the small cap 200 from the outside, and prevents a force delivered to the wing-type support unit wing from being distributed.

Also, the small cap upper surface through-hole 203, which is a circular opening that is formed at the upper end of the small cap 200, is formed to be smaller than an inner diameter of the small cap 200 and to be larger than an outer diameter of the needle fixing body 404 provided at the central portion of the hub 400 to be freely reciprocally moved through the needle fixing body 404, while the wing-type support unit 100, which is accommodated inside the wing-type support unit accommodation part 201 of the small cap 200, comes into contact with the wing-type support unit upper wing 103 and an inner side of the small cap upper surface 202, thereby moved downward with the small cap 200 when the small cap 200 is moved downward.

Figure 7:
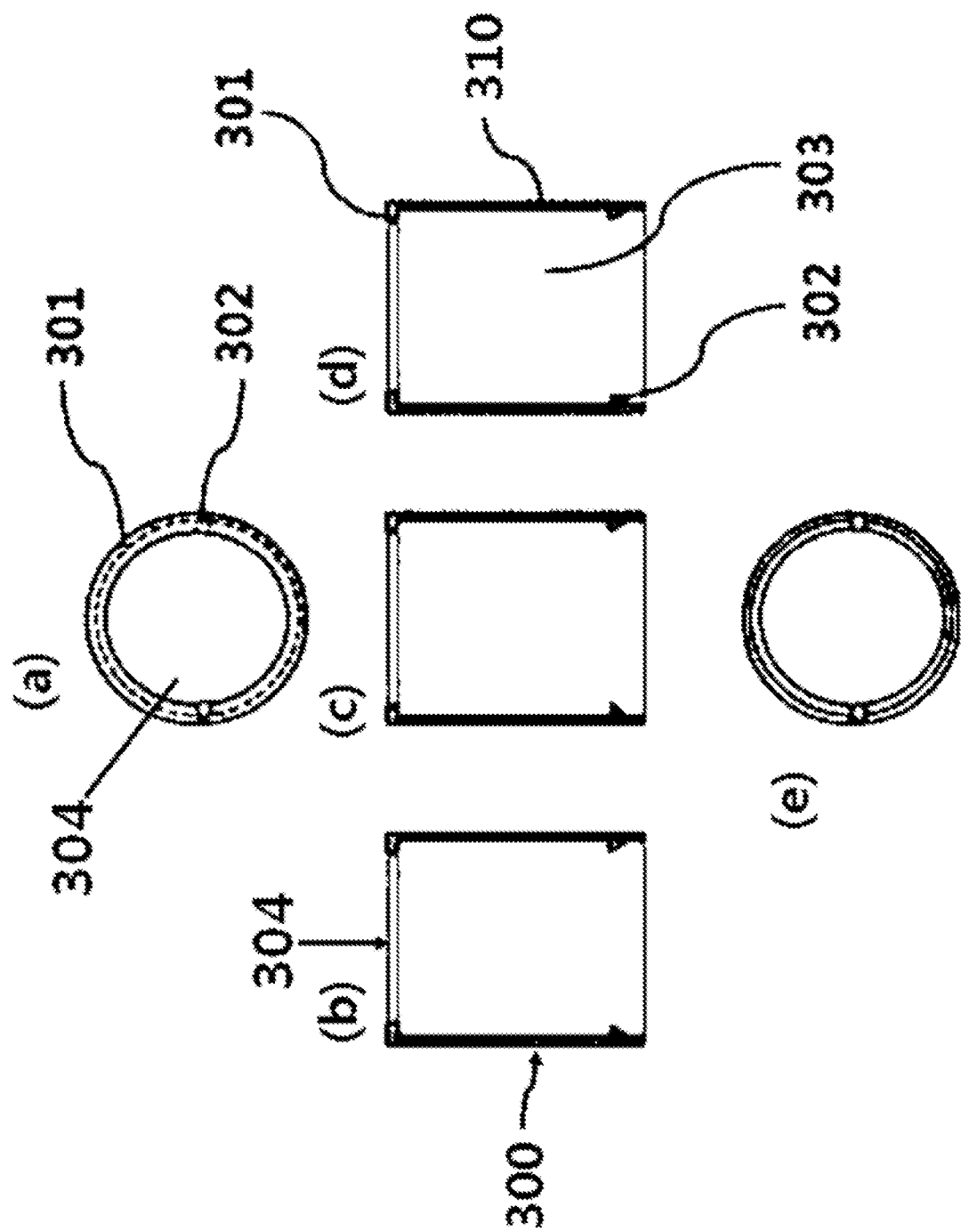
FIG. 7 is a cross sectional development view of a medium cap of FIG. 4.

FIG. 7 is a cross sectional development view of a medium cap of FIG. 4.

FIG. 7a is a diagram illustrating the medium cap 300 when viewed from a top side thereof, FIGS. 7b, 7c, and 7d are diagrams each illustrating the medium cap 300 when viewed from a left side, a front side, and a right side thereof, and FIG. 7e is a diagram illustrating the medium cap 300 when viewed from a bottom side thereof.

The medium cap 300 is configured to have a cylindrical shape. The medium cap 300 is configured such that a medium cap cylindrical wall body 310 having a cylindrical shape and a ring-shaped medium cap upper surface 301 having a circular-shaped medium cap upper surface through-hole 304 are connected to each other and installed therein. That is, the medium cap 300 is vertically open in a circular shape, and the medium cap upper surface through-hole 304, which is a circular opening of the upper end of the medium cap 300, is formed to be smaller than an inner diameter of the medium cap 300, to be larger than an outer diameter of the small cap cylindrical wall body 210, and to be smaller than the diameter of the small cap supporting plate 206, that is, an outer diameter of the small cap supporting plate wing-shaped protrusion 211. Consequently, the medium cap upper surface 301 prevents deviation of the small cap supporting plate 206, that is, the small cap supporting plate wing-shaped protrusion 211, through the medium cap upper surface through-hole 304. That is, deviation of the small cap 200 to the outside of the upper end of the medium cap 300 due to the elasticity of the spring is prevented. The medium cap upper surface 301 may be a medium cap upper surface ring-shaped bump.

The triangular-shaped medium cap bump 302 is formed at the lower portion of the inner side of the medium cap 300 to be engaged with the medium cap fixing recess 406 of the hub 400 so that the medium cap 300 and the hub 400 may be integrated. The medium cap 300 is configured with a structure and a form which are capable of internally accommodating all the wing-type support unit 100, the small cap 200 accommodating the wing-type support unit 100, the needle fixing body 404, and the spring 700.

Figure 8:
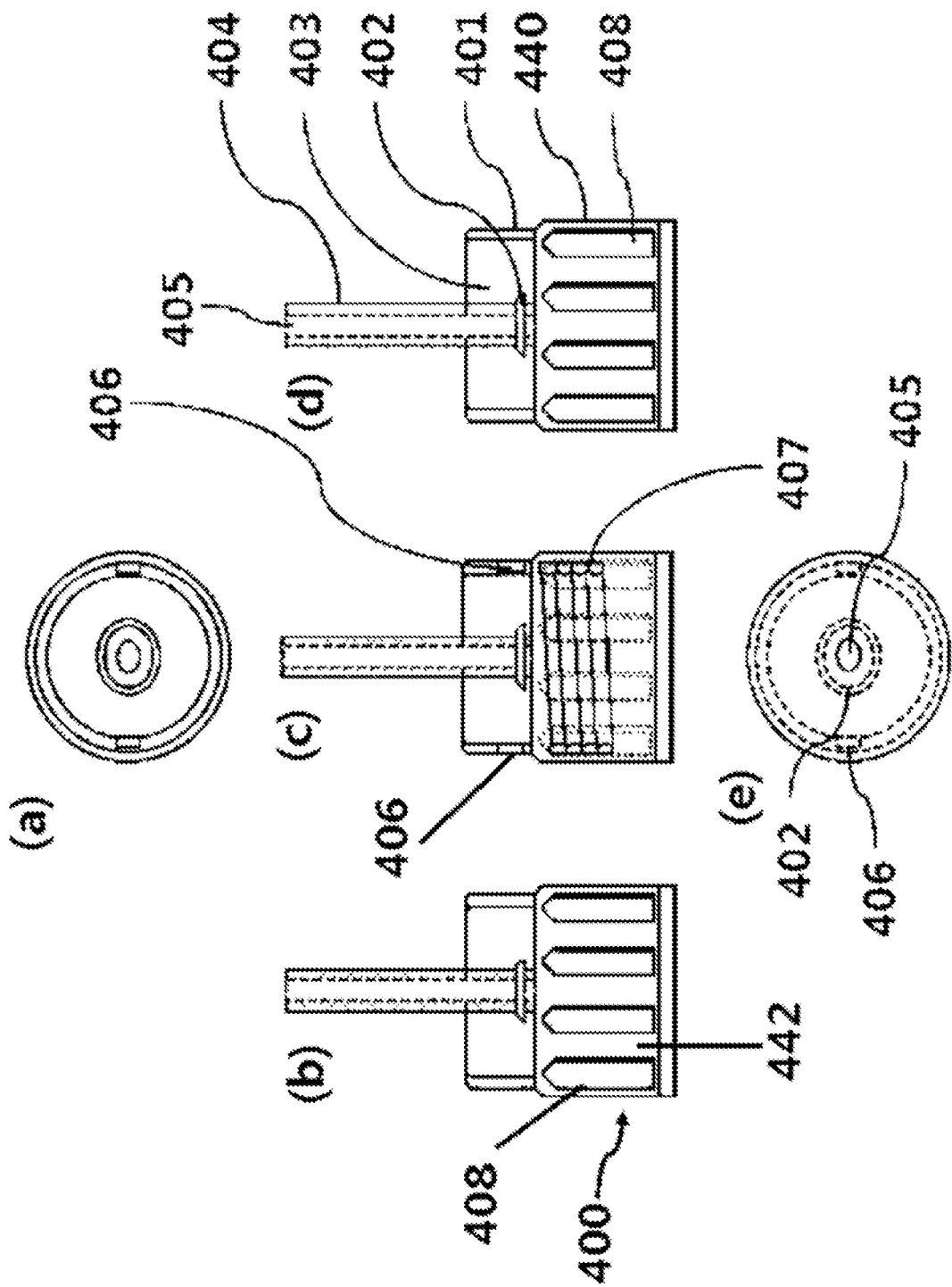
FIG. 8 is a cross sectional development view of a hub of FIG. 4.
Figure 9:
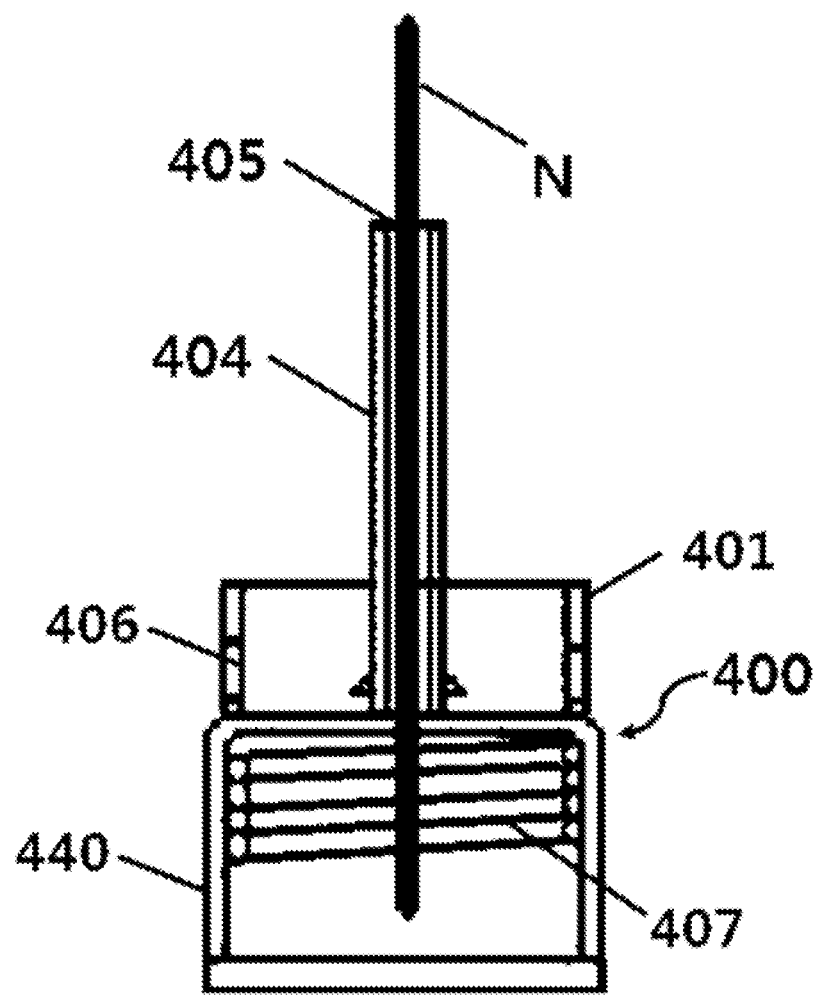
FIG. 9 is a diagram for describing a needle being mounted on the hub of FIG. 8.

FIG. 8 is a cross sectional development view of the hub 400 of FIG. 4, and FIG. 9 is a diagram for describing a needle N being mounted on the hub of FIG. 8.

FIG. 8a is a diagram illustrating the hub 400 when viewed from a top side thereof, FIGS. 8b, 8c, and 8d are diagrams each illustrating the hub 400 when viewed from a left side, a front side, and a right side thereof, and FIG. 8e is a diagram illustrating the hub 400 when viewed from a bottom side thereof.

The hub 400 is configured with the hub lower body 440, the needle fixing body 404, and the medium cap fixer 401.

A hub screw part 407 having a helically-shaped screw thread is provided at an inner side of the hub lower body 440 to be coupled to a syringe screw part 601. That is, the needle fixing body 404 is provided at the central portion of the hub 400, and the hub screw part 407 is provided to internally have the screw thread at an upper portion of an injection medication accommodation body so as to be couplable to the syringe screw part 601, which is provided at the upper portion of the injection medication accommodation body of a pen-type syringe.

A plurality of bar-shaped hub lower body protrusions 408 are provided at an outer side (that is, an external wall) of the hub lower body 440. A plurality of hub body recesses 442, which are each formed between every two of the plurality of hub lower body protrusions 408, are provided. Each of the plurality of hub body recesses 442 is coupled to a large cap internal protrusion 503 to engage the hub 400 with a large cap 500. That is, each of the plurality of hub lower body protrusions 408, which are provided at an external wall surface of a lower portion of the hub 400, and large cap internal protrusions 503, which are formed at a wall surface of a lower portion of an inner side of the large cap 500, intersect with and are coupled to each other to facilitate insertion and accommodation of the hub 400 inside the large cap 500 and to facilitate guidance of the hub 400 in an accurate insertion direction. That is, the plurality of hub lower body protrusions 408 are formed at the external wall of the hub lower body 440 in a band shape at regular intervals.

The needle fixing body 404 is located at the center of an upper end 430 of the hub lower body 440, and the hub lower body 440 and the needle fixing body 404 are stepped. A needle insertion through-hole 405 is provided at the center of an upper end of the needle fixing body 404 to enable the needle N to be inserted thereinto. The needle fixing body bump 402 is provided at the lower portion of the needle fixing body 404, and the needle fixing body bump 402 is coupled to the wing-type support unit lower bump 104. The spring 700 is mounted at the outer side of the needle fixing body 404, and the small cap 200 is mounted over the spring 700.

In some cases, the needle fixing body bump 402 may be configured with a partially protruding protrusion or bump instead of the ring-shaped bump, and, in this case, the protrusion or bump (not shown) may be coupled to the wing-type support unit recess 109.

The medium cap fixer 401 is provided at the upper surface rim of the hub lower body 440 in a rounded fence-like shape. The medium cap fixing recess 406 in a shape of a through-hole recess is provided at the medium cap fixer 401. The medium cap 300 is mounted at the outer side of the medium cap fixer 401, and the medium cap fixing recess 406 is coupled to the medium cap bump 302 provided at the lower portion of the inner side of the medium cap 300 to engage the hub 400 with the medium cap 300.

A spring insertion and accommodation hole 403, which is a space capable of accommodating the spring 700, is provided between the medium cap fixer 401 and the needle fixing body 404.

As shown in FIG. 9, the needle is inserted into the needle insertion through-hole 405 of the needle fixing body 404. Conventionally, a needle N that is exposed to outside the needle fixing body 404 is called a front needle, and a needle N that is located inside the hub and is inserted into an injection medication accommodation body 602 of a pen-type syringe main body 605 is called a rear needle.

Figure 10:
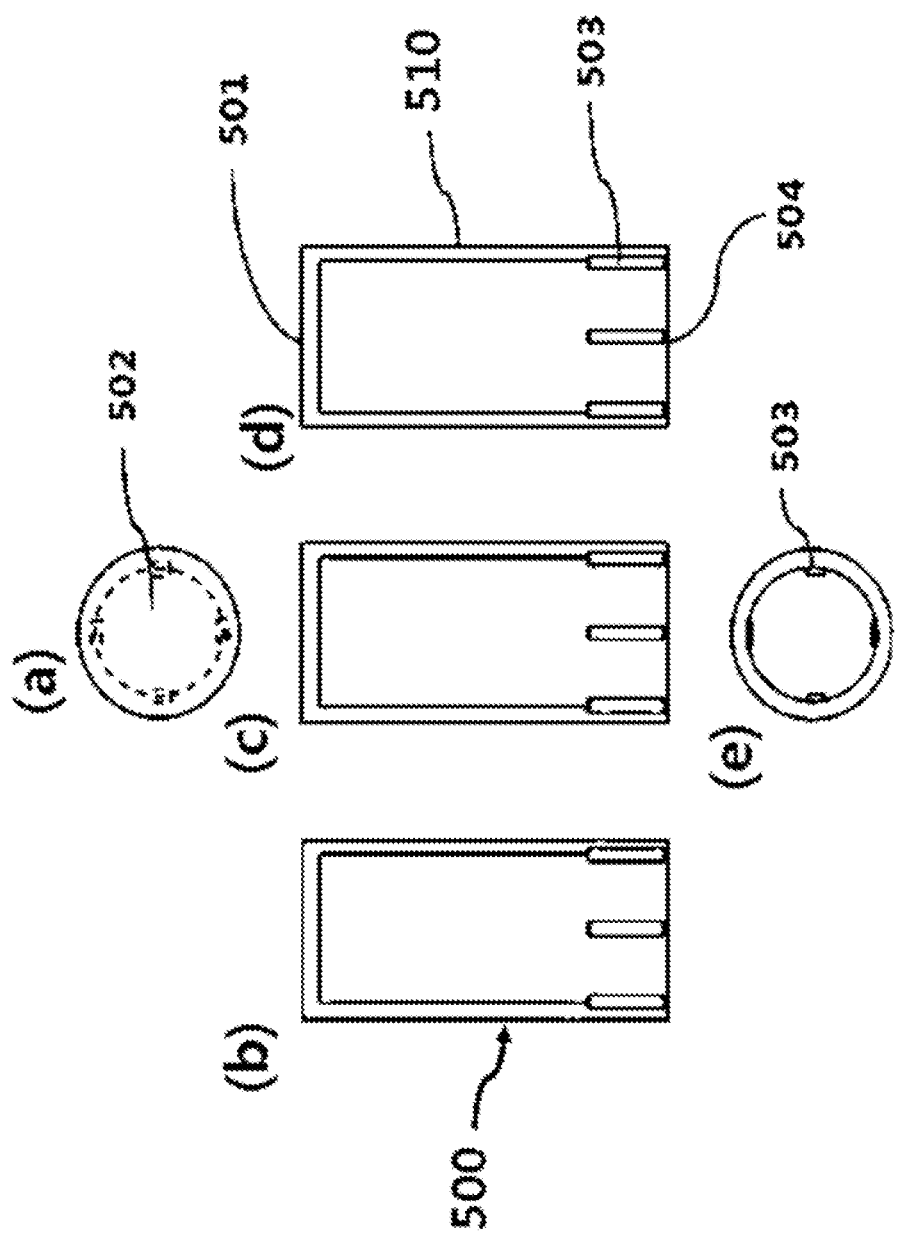
FIG. 10 is a cross sectional development view of a large cap 500.

FIG. 10 is a cross sectional development view of the large cap 500.

FIG. 10a is a diagram illustrating the large cap 500 when viewed from a top side thereof, FIGS. 10b, 10c, and 10d are diagrams each illustrating the large cap 500 when viewed from a left side, a front side, and a right side thereof, and FIG. 10e is a diagram illustrating the large cap 500 when viewed from a bottom side thereof.

The large cap 500 is totally in the form of a cylindrical pillar shape, and is configured such that a large cap cylindrical wall body 510 and a large cap upper surface 501 are connected to each other and installed therein. An upper end of the large cap 500 is blocked by the large cap upper surface 501 having a circular plate shape, and a lower end thereof is provided with a large cap lower opening 504, which is a through-hole. The large cap internal protrusion 503 is provided at a lower portion of an inner side of the large cap cylindrical wall body 510.

That is, the upper end of the large cap 500 is blocked, the large cap lower opening 504 is formed at the lower end of the large cap 500, a hub assembly accommodation part 502 is provided at the large cap 500 to accommodate all the small cap 200 accommodating the wing-type support unit 100, the medium cap 300, and the hub 400, and a bottom surface of the large cap lower opening 504 is press-sealed with a sterilized sheet finishing material 290 so that the large cap 500 is ultimately sterilized by ethylene oxide (EO) gas.

Figure 11:
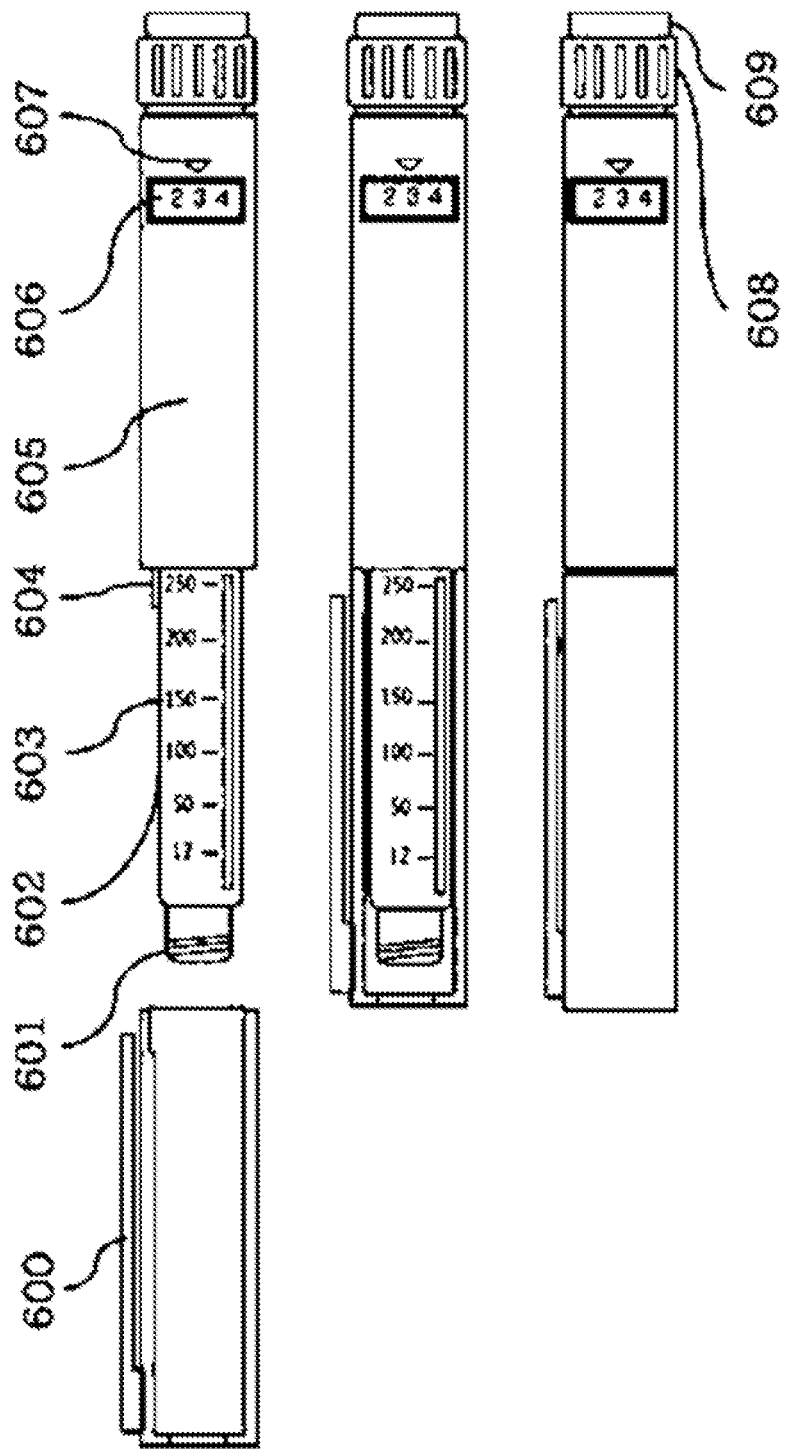
FIG. 11 is a diagram for describing a conventional pen-type syringe and a role of a cover thereof.

FIG. 11 is a diagram for describing a conventional pen-type syringe and a role of a cover thereof.

Generally, a pen-type syringe is configured with a pen-type syringe cover 600 and a pen-type syringe main body 605, an injection medication accommodation body 602 is provided inside the pen-type syringe main body 605 to accommodate an injection medication therein, and a syringe screw part 601 is provided at the injection medication accommodation body 602 to be couplable to a hub 400 in a screw-coupling manner. Also, an injection medication dosage scale 603 is presented on the pen-type syringe main body 605 to enable a user to verify a dosage of the injection medication, and an injection medication setting verification scale window 606 and an injection medication setting revolving lever 608 are provided to enable the user to set an injection dosage of the injection medication according to a prescription of a doctor. In addition, an injection medication administration push button 609 is provided at the pen-type syringe main body 605 so that, after a pen needle and the pen-type syringe main body 605 are coupled to and engaged with each other, the user may press the injection medication administration push button 609 to administer the injection medication that is set by the injection medication setting revolving lever 608.

FIGS. 12 to 15 are diagrams for describing an assembly order of each component of the pen needle provided with a safety protection system according to the first embodiment of the present disclosure.

Figure 12:
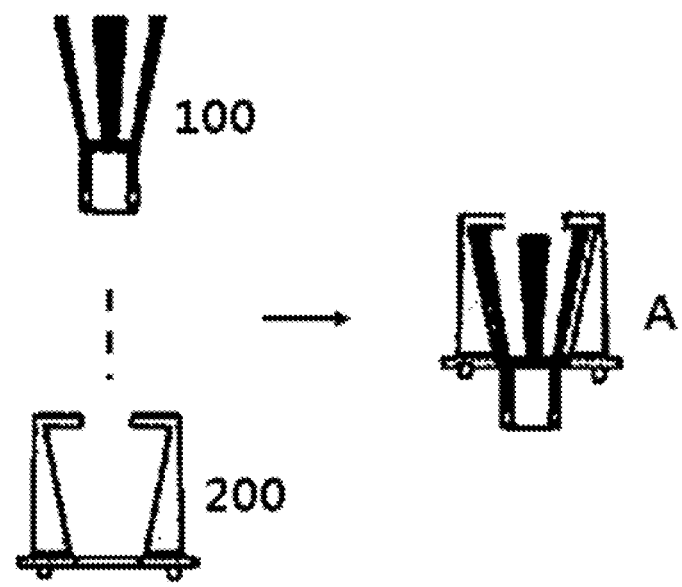
FIGS. 12 to 15 are diagrams for describing an assembly order of each component of the pen needle provided with the safety protection system according to the first embodiment of the present disclosure.

As shown in FIG. 12, the wing-type support unit 100 is inserted into the small cap upper surface through-hole 203 of the small cap 200 to be coupled to the small cap 200.

Figure 13:
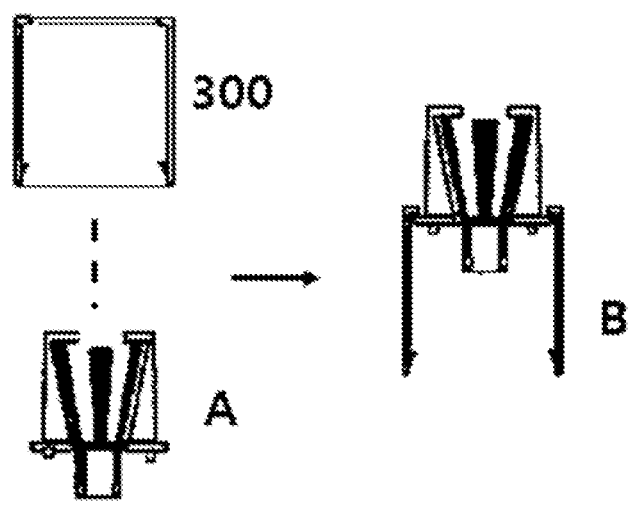

As shown in FIG. 13, the medium cap 300 is mounted over the small cap 200 accommodating the wing-type support unit 100, that is, over a configuration A in which the wing-type support unit 100 and the small cap 200 are coupled to each other, and, as shown in a configuration B of FIG. 13, the medium cap 300 is mounted such that a portion of the small cap cylindrical wall body 210 protrudes through the medium cap upper surface through-hole 304, and the small cap supporting plate 206 is located below the medium cap upper surface 301.

Figure 14:
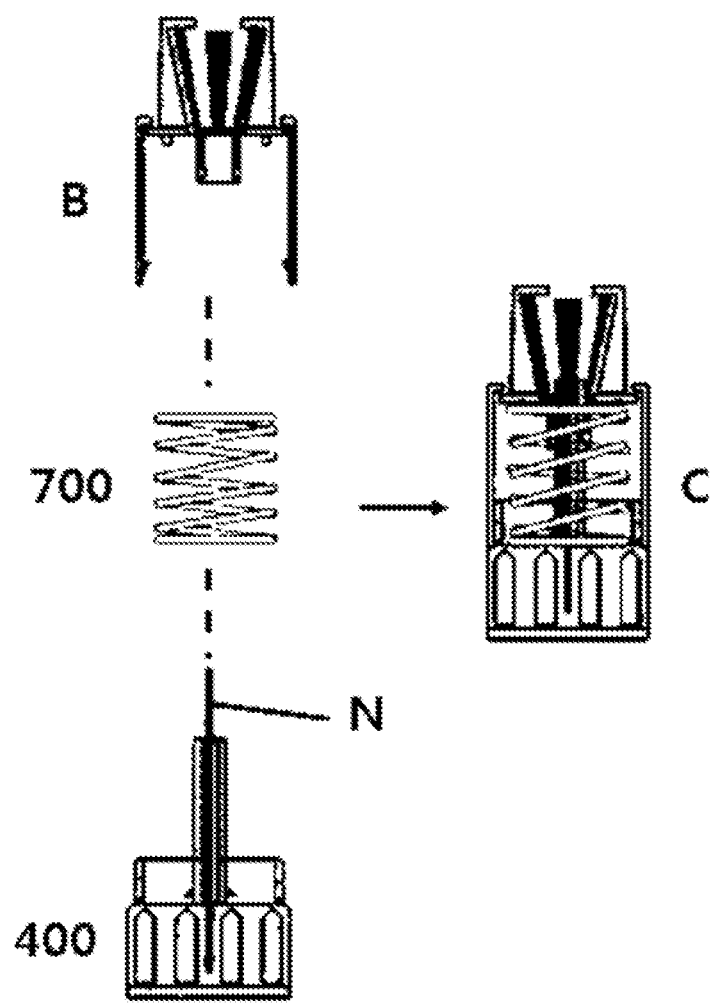

As shown in FIG. 14, the spring 700 is fitted on the needle fixing body 404 of the hub 400 on which the needle N is mounted to be coupled to the configuration B, in which the wing-type support unit 100, the small cap 200, and the medium cap 300 are coupled. At this point, the medium cap fixing recess 406 provided at the medium cap fixer 401 of the hub 400 is coupled to the medium cap bump 302 of the medium cap 300 to engage the hub 400 with the medium cap 300. In other words, the medium cap 300 coupled to the wing-type support unit 100 and the small cap 200 is engaged with the hub 400, in which the spring 700 is fitted on the needle fixing body 404.

Figure 15:
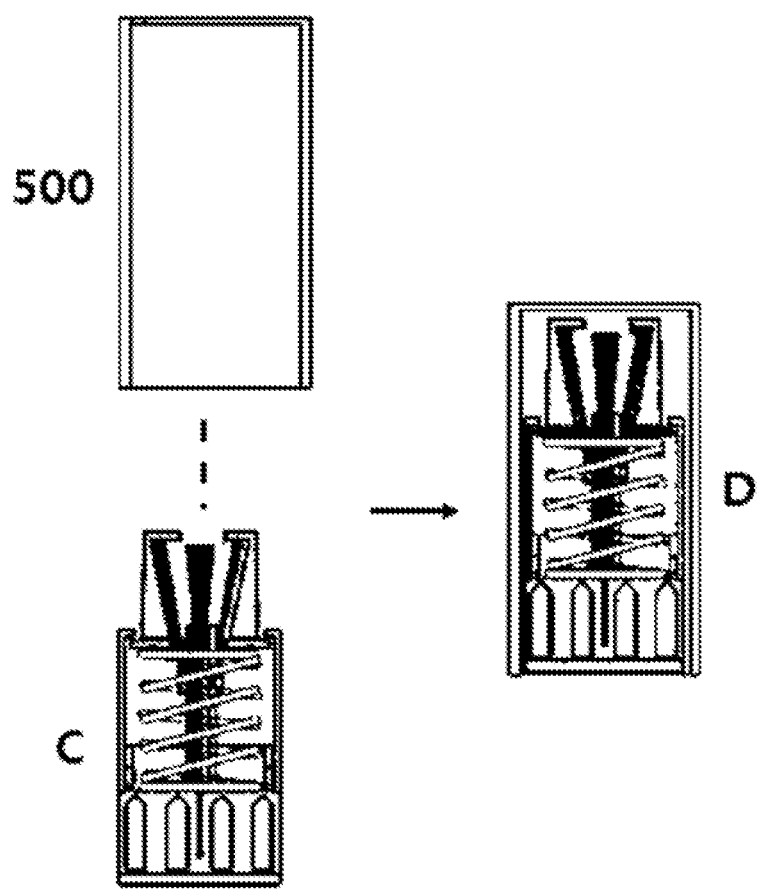

As shown in FIG. 15, the large cap 500 is mounted over a configuration C in which the hub 400, the wing-type support unit 100, the small cap 200, the medium cap 300, and the spring 700 are coupled. At this point, the hub body recess 442 of the hub 400 is coupled to the large cap internal protrusion 503 of the large cap 500 to engage the hub 400 with the large cap 500. Subsequently, the large cap lower opening 504 is sealed with a sterilized finishing sheet and then a sterilization process is performed using EO gas to commercialize a product.

In the first embodiment of the present disclosure, the hub 400, the wing-type support unit 100, the small cap 200, the medium cap 300, the spring 700, and the large cap 500 are packaged and coupled to manufacture a pen needle.

Figure 16:
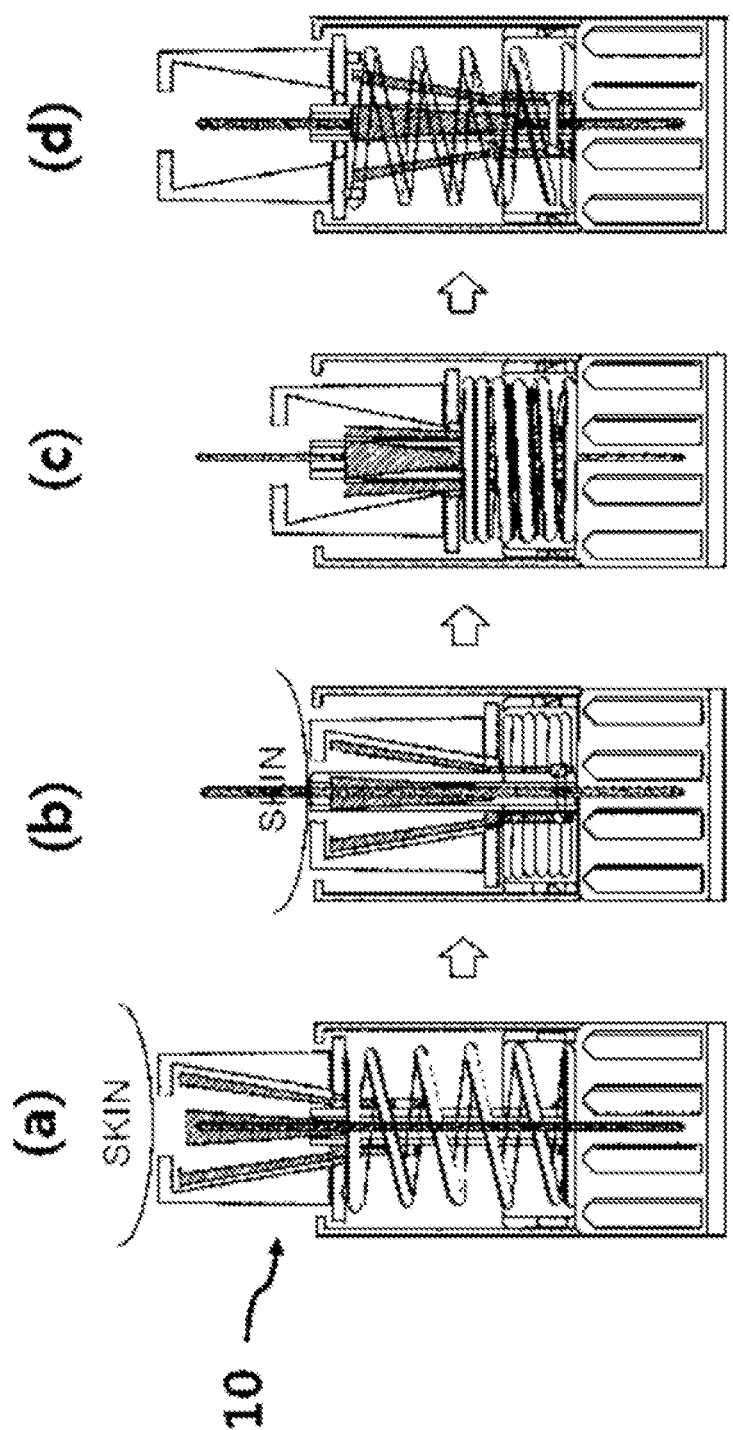
FIG. 16 is a diagram for describing an operation of the pen needle provided with the safety protection system according to the first embodiment of the present disclosure.

FIG. 16 is a diagram for describing an operation of the pen needle provided with a safety protection system according to the first embodiment of the present disclosure.

A pen needle 10 comes into contact with the skin of a user, as shown in FIG. 16a, and the needle N protrudes outside the small cap 200 to pierce the skin when the injection medication administration push button 609 is pressed, as shown in FIG. 16b, such that an injection medication is administered. That is, as shown in FIG. 16b, the spring 700 is contracted due to a pressing pressure and the wing-type support unit 100 is blocked by the small cap upper surface 202 while the needle fixing body 404 of the hub 400 is moved upward such that the needle N mounted on the needle fixing body 404 enters the skin. At this point, as the spring 700 is contracted, the needle fixing body bump 402 of the hub 400 is coupled to the wing-type support unit lower bump 104 of the wing-type support unit 100 or to the wing-type support unit recess 109.

When the injection medication administration push button 609 is released after the administration of the injection medication is completed, as shown in FIG. 16c, the contracted spring 700 stretches to push the small cap supporting plate 206 upward so that, as the spring 700 is restored, the small cap 200 is moved upward. At this point, as shown in FIG. 16d, the needle fixing body bump 402 and the wing-type support unit lower bump 104 which are coupled or the needle fixing body bump 402 and the wing-type support unit recess 109 which are coupled are maintained in a coupled state.

Consequently, as shown in FIG. 16d, the wing-type support unit 100 is located below the small cap supporting plate 206. At this point, the wing-type support unit blocking bump 205 provided at the bottom surface of the small cap supporting plate 206 blocks the wing-type support unit wing 108 from being unfolded further.

That is, in FIG. 16d, the small cap 200 is fully lifted up to the medium cap upper surface 301 inside the medium cap 300 due to an elastic restoring force of the spring so that the wing-type support unit upper wing 103, which is made of an elastic material and is accommodated inside the wing-type support unit accommodation part 201 of the small cap 200, is completely separated from the wing-type support unit insertion through-hole 204 provided at a lower end of the small cap 200 to deviate downwardly therefrom, and then the wing-type support unit 100 is restored again in an unfolded shuttlecock shape due to self-elasticity such that the wing-type support unit blocking bump 205 provided at a lower end portion of the small cap 200 blocks the unfolding of wing-type support unit wing 108 and the small cap 200 is not further moved downward again when the pressing pressure is externally applied. Consequently, the wing-type support unit 100 is located and fixed below the small cap supporting plate 206 so that the spring does not stretch any further and the needle is fixed inside the small cap 200. Therefore, the needle cannot be used again.

Figure 17:
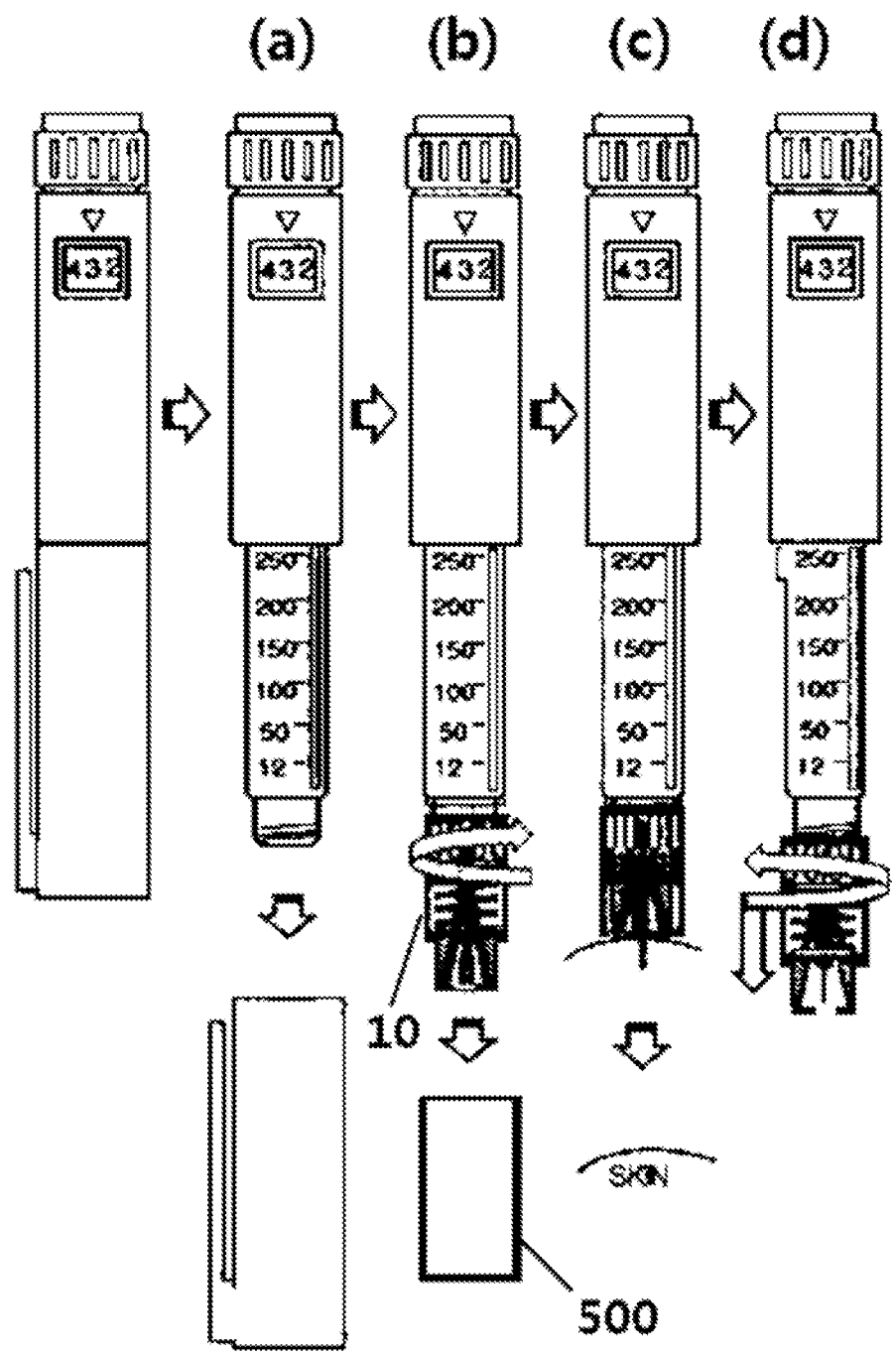
FIG. 17 is a diagram for describing a method of applying and using the pen needle according to the first embodiment of the present disclosure to a pen-type syringe.

FIG. 17 is a diagram for describing a method of applying and using the pen needle according to the first embodiment of the present disclosure to a pen-type syringe.

The pen-type syringe cover 600 is separated from the pen-type syringe main body 605, as shown in FIG. 17a, the sterilized finishing sheet is removed from the pen needle 10 of the present disclosure, as shown in FIG. 17b, and then the pen needle 10 is coupled to and engaged with the syringe screw part 601 of the pen-type syringe main body 605 in a screw coupling manner and the large cap 500 is removed. The hub 400 is rotated (for example, in a clockwise direction) to screw-couple the hub 400 of the pen needle 10 to the pen-type syringe main body 605.

As shown in FIG. 17c, administration of an injection medication using the pen needle 10 coupled to the pen-type syringe main body 605 is performed through the same operation as in FIGS. 16a to 16d. After the administration of the injection medication is completed, like in FIG. 16d, the wing-type support unit 100 is located and fixed below the small cap supporting plate 206 so that the spring does not stretch any further and the needle is fixed inside the small cap 200 to be prevented from being reused.

As shown in FIG. 17d, the pen needle 10 which has completed administration of the injection medicine is rotated in a reverse direction (for example, a counterclockwise direction) compared to when the pen needle 10 was coupled to the pen-type syringe main body 605 to remove the pen needle 10 from the pen-type syringe main body 605.

As is described above, a one-time use pen needle provided with a safety protection system is safely discarded, and the user couples the pen-type syringe cover 600 to the pen-type syringe main body 605 to be stored until a next time of use.

Figure 18:
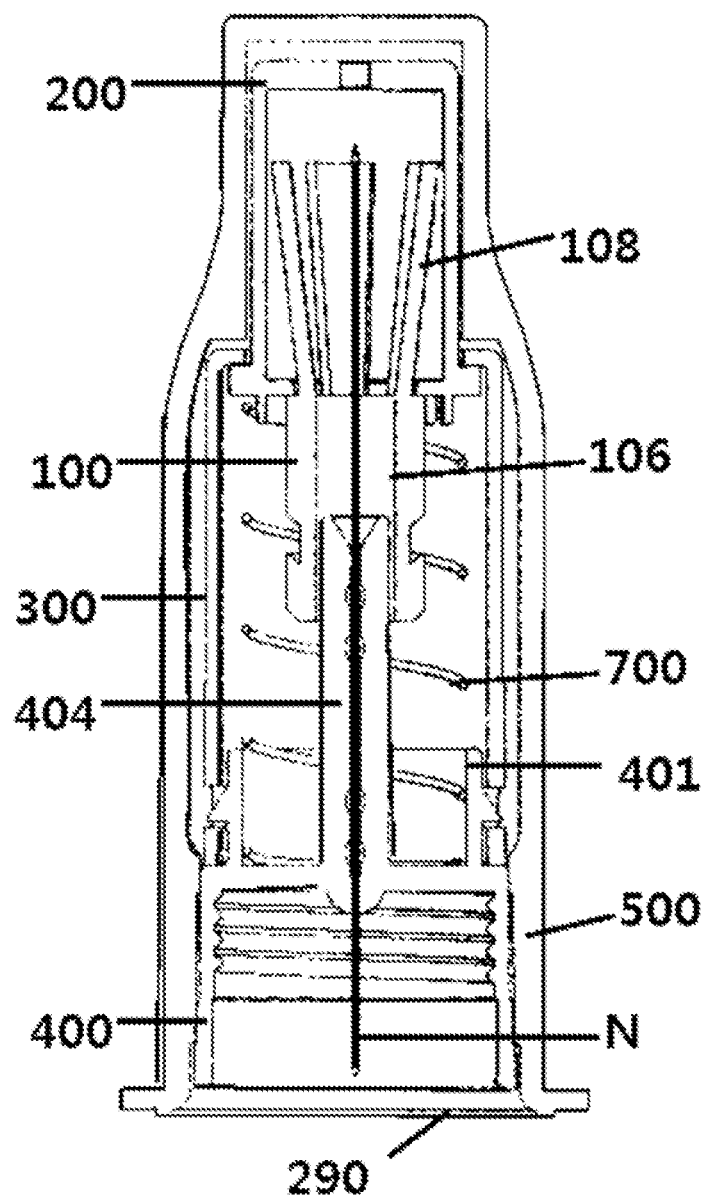
FIG. 18 is a diagram for schematically describing a configuration of a pen needle provided with a safety protection system according to a second embodiment of the present disclosure.
Figure 19:
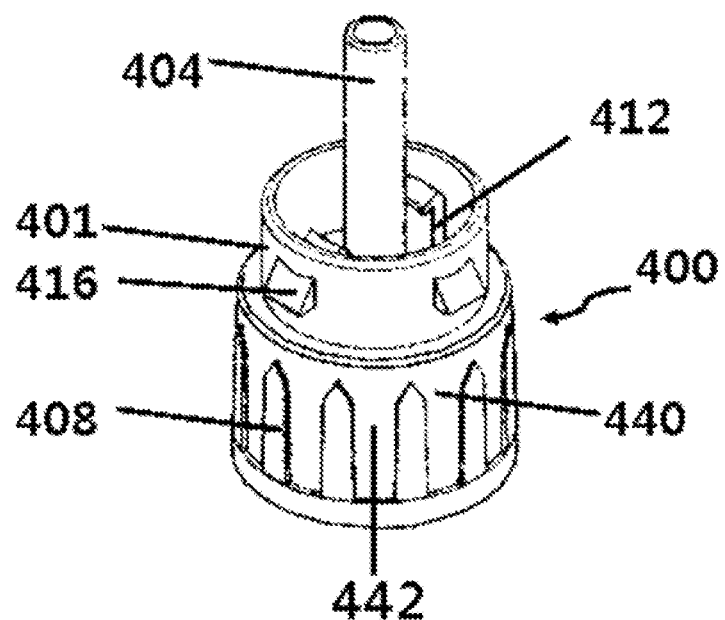
FIG. 19 is a diagram illustrating a hub 400 of FIG. 18.
Figure 20:
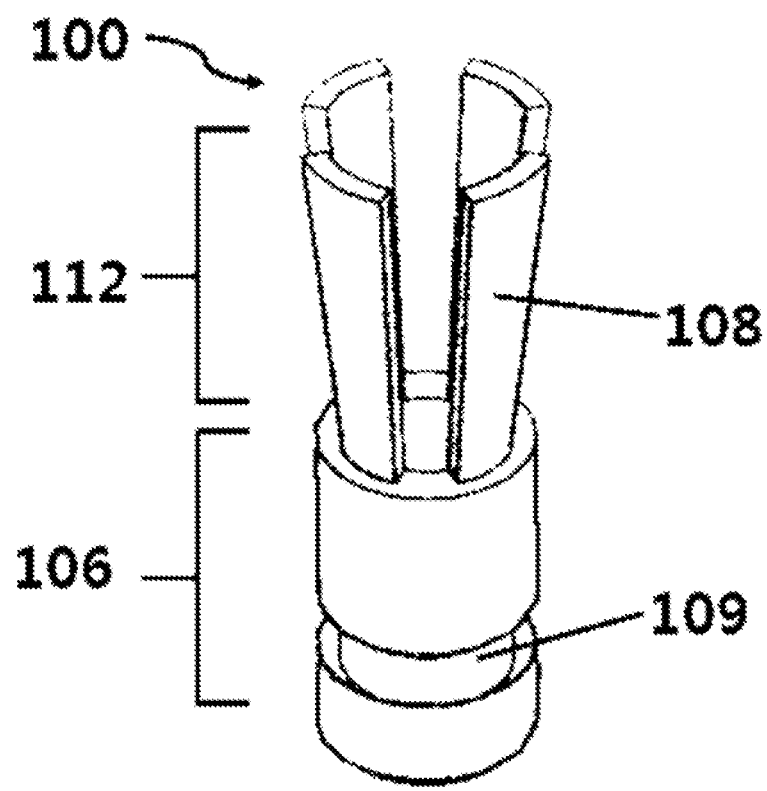
FIG. 20 is a diagram illustrating a wing-type support unit 100 of FIG. 18.
Figure 21:
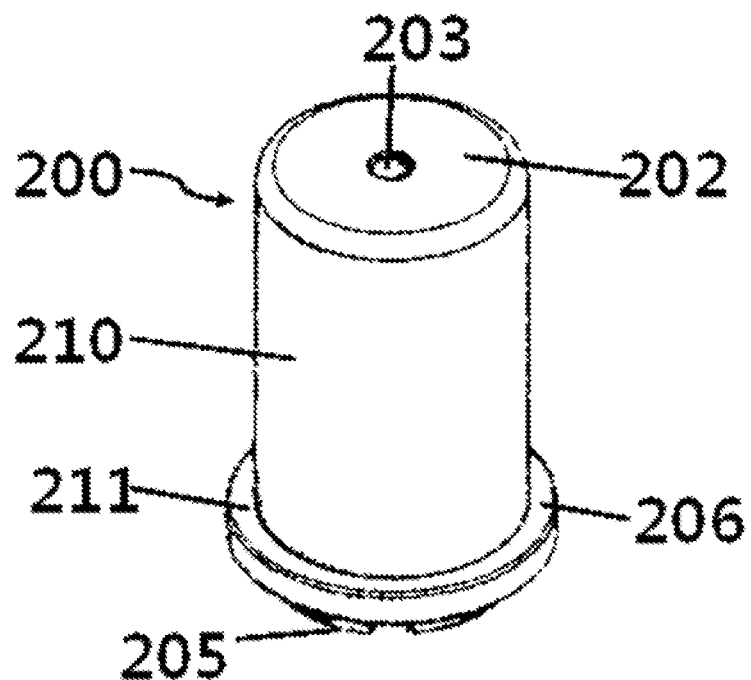
FIG. 21 is a diagram illustrating a small cap 200 of FIG. 18.
Figure 22:
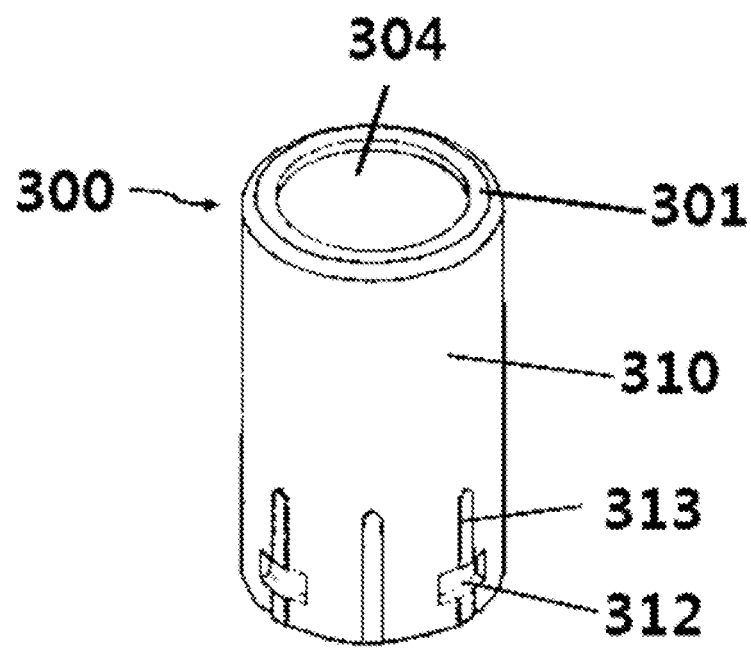
FIG. 22 is a diagram illustrating a medium cap 300 of FIG. 18.
Figure 23:
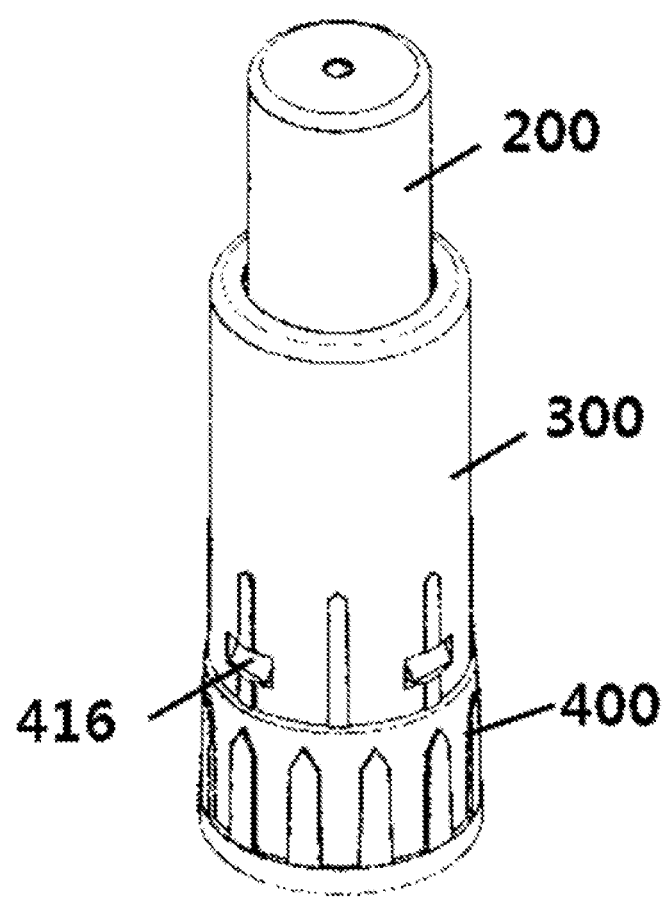
FIG. 23 is a diagram illustrating a coupled state of the wing-type support unit, the medium cap, the small cap, and the hub.
Figure 24:
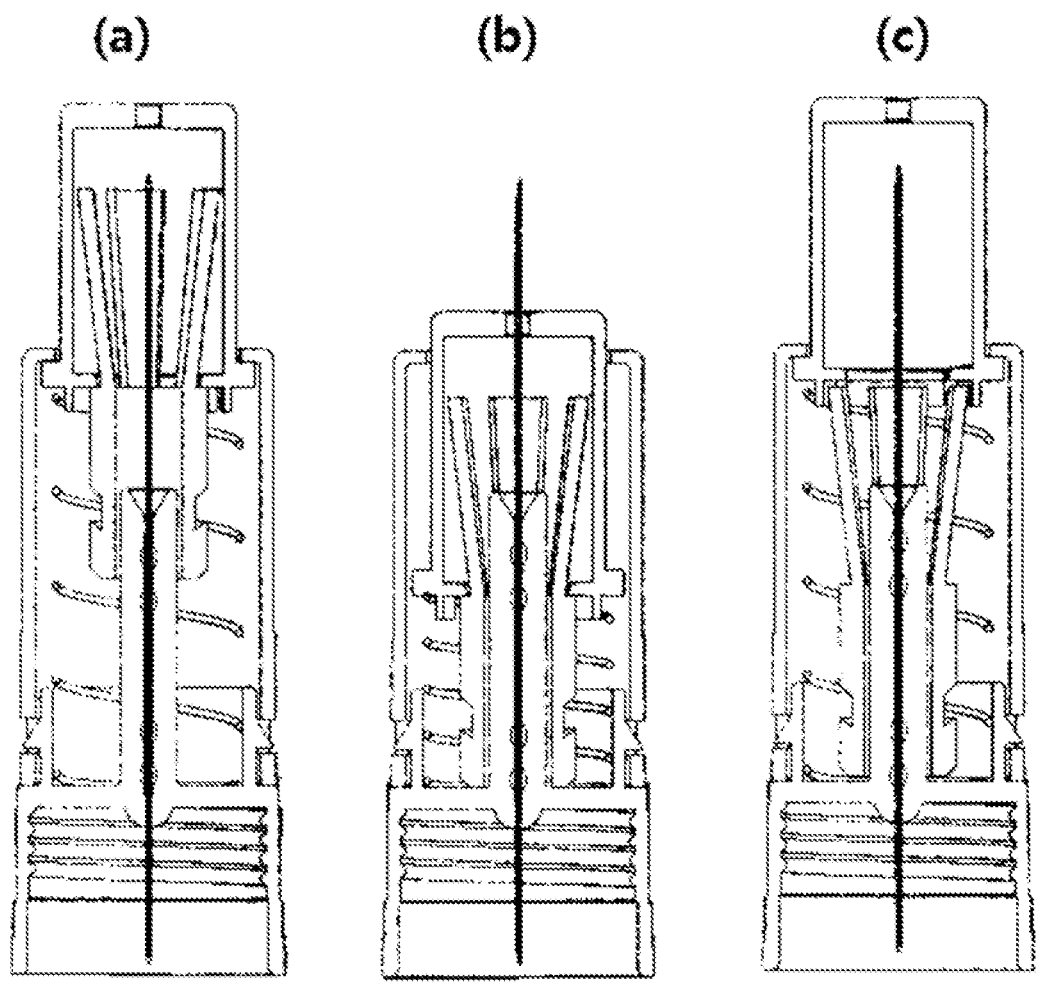
FIG. 24 is a diagram for describing an operation of the pen needle provided with the safety protection system according to the second embodiment of the present disclosure.

FIG. 18 is a diagram for schematically describing a configuration of a pen needle provided with a safety protection system according to a second embodiment of the present disclosure, FIG. 19 is a diagram illustrating a hub 400 of FIG. 18, FIG. 20 is a diagram illustrating a wing-type support unit 100 of FIG. 18, FIG. 21 is a diagram illustrating a small cap 200 of FIG. 18, FIG. 22 is a diagram illustrating a medium cap 300 of FIG. 18, FIG. 23 is a diagram illustrating a coupled state of the wing-type support unit, the medium cap, the small cap, and the hub, and FIG. 24 is a diagram for describing an operation of the pen needle provided with a safety protection system according to the second embodiment of the present disclosure.

The pen needle according to the second embodiment of the present disclosure has a configuration almost similar to that of the pen needle according to the first embodiment. Different portions will be described below.

Comparing the hub 400 of the second embodiment with the hub 400 of the first embodiment, the hub 400 of the first embodiment is provided with the medium cap fixing recess 406 and the needle fixing body bump 402, whereas, as shown in FIG. 19, the hub 400 of the second embodiment is provided with a medium cap fixing bump 416 and a wing-type support unit fixer 412. Except for the above-described components, the configuration of the hub 400 of the second embodiment is the same as that of the hub 400 of the first embodiment.

The medium cap fixing bump 416 of FIG. 19 is coupled to a medium cap body recess 312 to engage the medium cap 300 with the hub 400.

Also, the wing-type support unit fixer 412 of FIG. 19 is configured to have a hook shape to be coupled to the wing-type support unit recess 109 of the wing-type support unit 100. A function of the wing-type support unit fixer 412 is the same as that of the needle fixing body bump 402.

The wing-type support unit 100 of FIG. 20 is the same as the wing-type support unit 100 of the first embodiment. Therefore, a detailed description thereof will be omitted. When the injection medication administration push button 609 is pressed, the wing-type support unit 100 is moved below the small cap supporting plate 206 so that the wing-type support unit fixer 412 having the hook shape is hooked to the wing-type support unit recess 109.

The small cap 200 of FIG. 21 is the same as the small cap 200 of the first embodiment. Therefore, a detailed description thereof will be omitted.

Comparing the medium cap 300 of the second embodiment with the medium cap 300 of the first embodiment, the medium cap 300 of the first embodiment is provided with the medium cap bump 302, whereas, as shown in FIG. 22, the medium cap 300 of the second embodiment is provided with the medium cap body recess 312. The medium cap body recess 312 is coupled to the medium cap fixing bump 416 of the hub to engage the medium cap with the hub.

Also, the medium cap 300 may also be provided with a medium cap external protrusion 313, and the medium cap external protrusion 313 enables the large cap 500 and the medium cap 300 to be spaced a constant distance apart.

FIG. 23 shows that the small cap, the wing-type support unit 100, and the medium cap are coupled, and this coupled configuration is coupled to the hub 400 in which the spring 700 is fitted on the needle fixing body 404.

FIG. 24a is the same as FIG. 16a, and, for the purpose of performing injection, the pen needle 10 comes into contact with the skin of a user.

FIG. 24b is the same as FIG. 16b, the needle N protrudes outside the small cap 200 to pierce the skin when the injection medication administration push button 609 is pressed such that an injection medication is administered. That is, as shown in FIG. 24b, the spring 700 is contracted due to a pressing pressure and the wing-type support unit 100 is blocked by the small cap upper surface 202 while the needle fixing body 404 of the hub 400 is moved upward such that the needle N mounted on the needle fixing body 404 enters the skin. At this point, as the spring 700 is contracted, the wing-type support unit fixer 412 configured in a hook shape is coupled to the wing-type support unit recess 109 of the wing-type support unit 100 inside the hub 400.

FIG. 24c is the same as FIG. 16d. That is, when the injection medication administration push button 609 is released after administration of the injection medication is completed, the contracted spring 700 stretches to push the small cap supporting plate 206 upward so that, as the spring 700 is restored, the small cap 200 is moved upward and the wing-type support unit 100 is located below the small cap supporting plate 206. At this point, the wing-type support unit fixer 412 having the hook shape of the hub 400 is hooked to the wing-type support unit 100 and the wing-type support unit recess 109.

As a result, the wing-type support unit upper wing 103, which is made of an elastic material and is accommodated inside the wing-type support unit accommodation part 201 of the small cap 200, is completely separated from the wing-type support unit insertion through-hole 204 provided at the lower end of the small cap 200 to deviate downwardly therefrom, and then the wing-type support unit 100 is restored again in an unfolded shuttlecock shape due to self-elasticity such that the wing-type support unit blocking bump 205 provided at the lower end portion of the small cap 200 blocks the wing-type support unit wing 108 from unfolding, and the small cap 200 is not further moved downward again when the pressing pressure is externally applied. Consequently, the wing-type support unit 100 is located and fixed below the small cap supporting plate 206 so that the spring does not stretch any further and the needle is fixed inside the small cap 200. Therefore, the needle cannot be used again.

Figure 25:
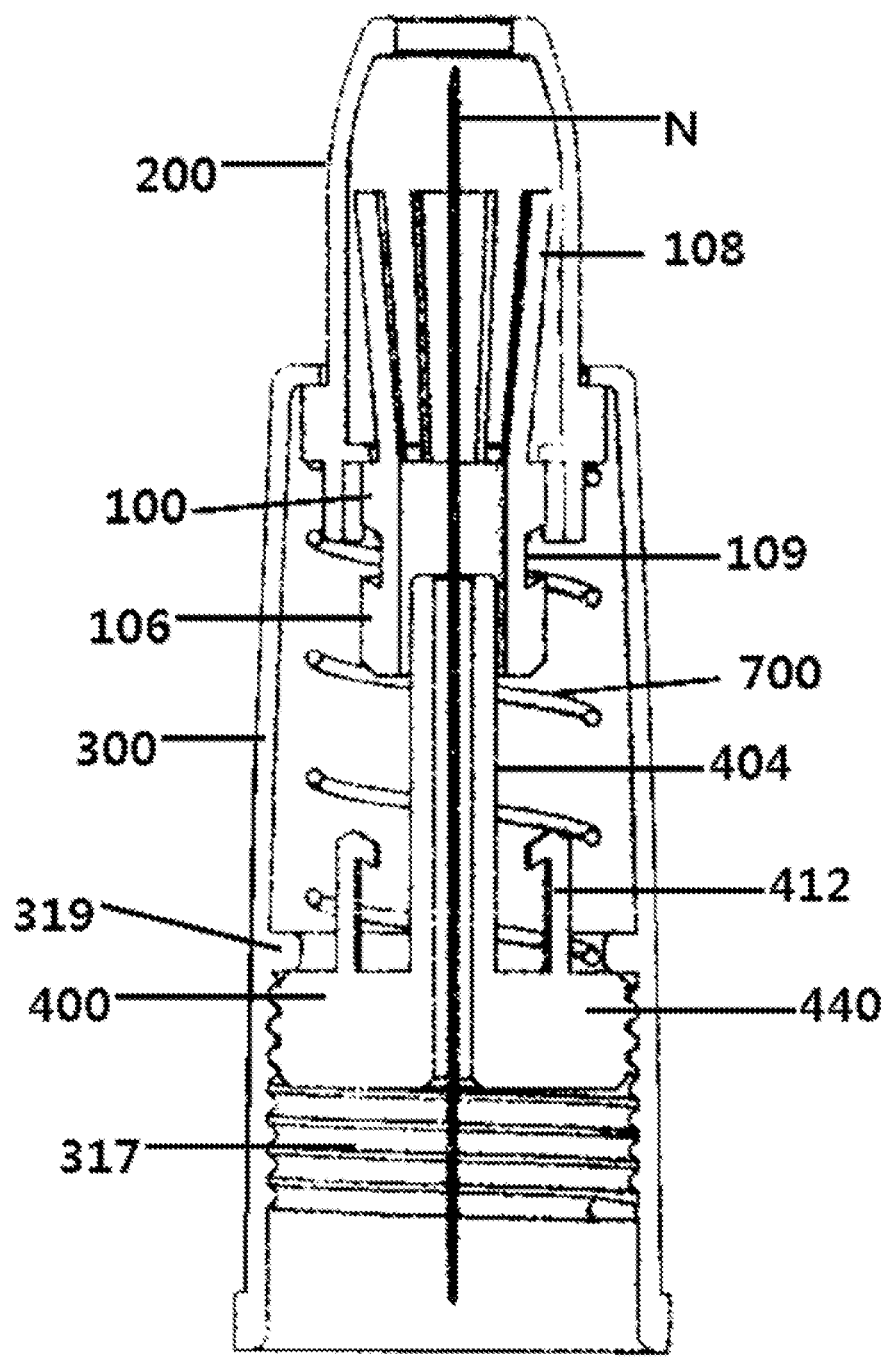
FIG. 25 is a diagram for schematically describing a configuration of a pen needle provided with a safety protection system according to a third embodiment of the present disclosure.
Figure 26:
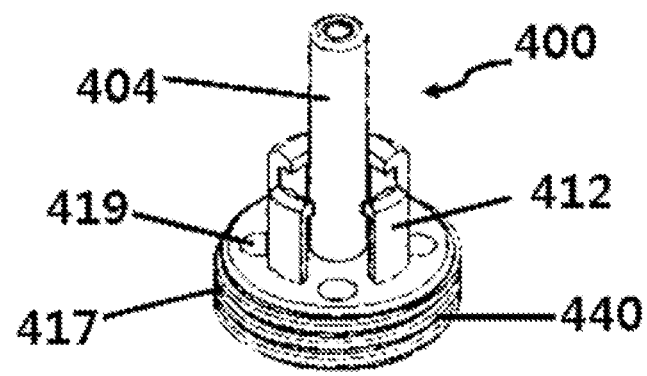
FIG. 26 is a diagram illustrating a hub 400 of FIG. 25.
Figure 27:
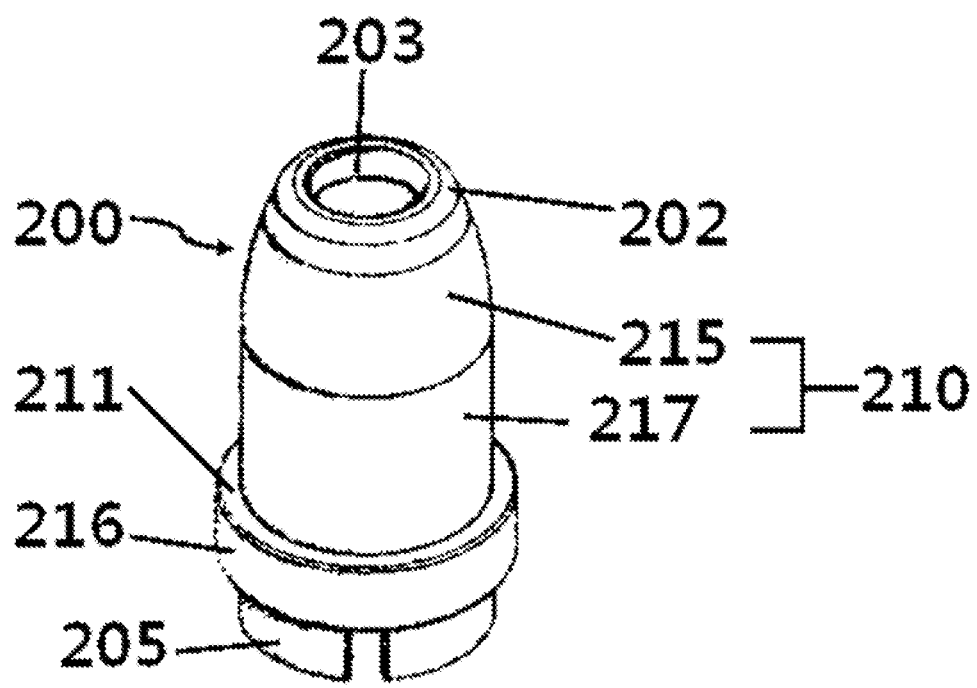
FIG. 27 is a diagram illustrating a small cap 200 of FIG. 25.
Figure 28:
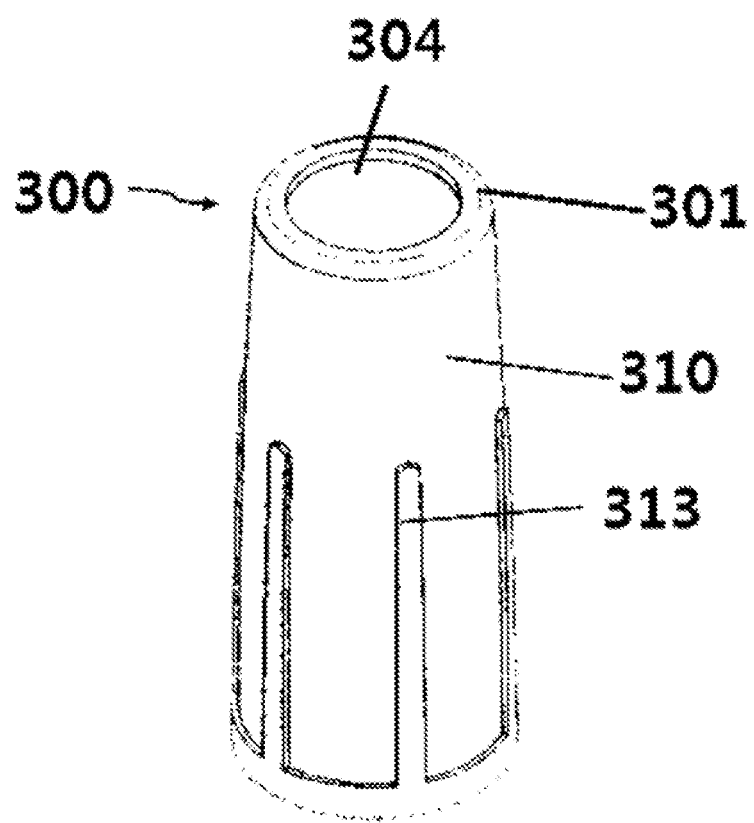
FIG. 28 is a diagram illustrating a medium cap 300 of FIG. 25.
Figure 29:
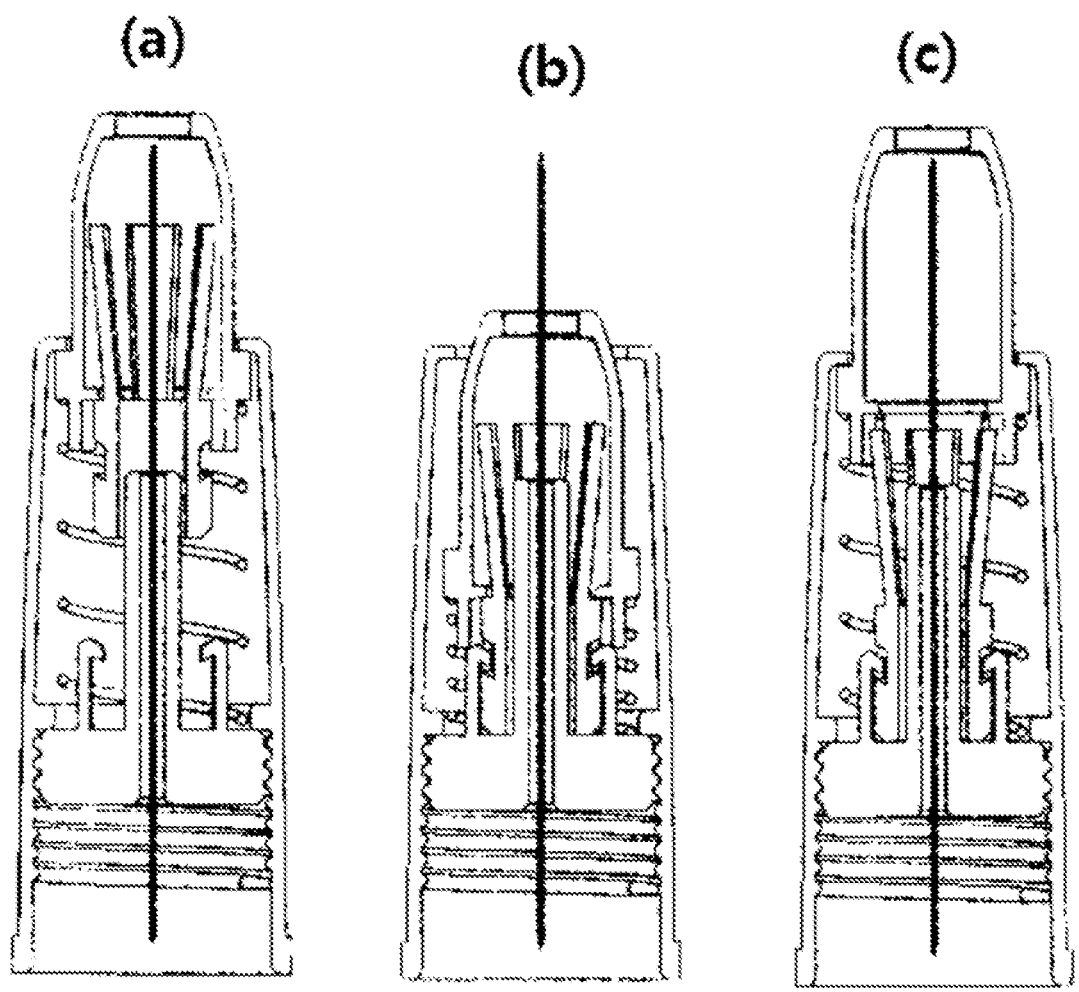
FIG. 29 is a diagram for describing an operation of the pen needle provided with the safety protection system according to the third embodiment of the present disclosure.

FIG. 25 is a diagram for schematically describing a configuration of a pen needle provided with a safety protection system according to a third embodiment of the present disclosure, FIG. 26 is a diagram illustrating a hub 400 of FIG. 25, FIG. 27 is a diagram illustrating a small cap 200 of FIG. 25, FIG. 28 is a diagram illustrating a medium cap 300 of FIG. 25, and FIG. 29 is a diagram for describing an operation of the pen needle provided with the safety protection system according to the third embodiment of the present disclosure.

A wing-type support unit 100 of the third embodiment is the same as the wing-type support unit 100 of each of the first embodiment and the second embodiment.

In the third embodiment, the medium cap 300 performs some functions of the hub 400.

In the case of the third embodiment, a hub outer wall screw part 417 is provided at a lateral surface of the hub lower body 440 and is engaged with a medium cap screw part 317 provided at a lower portion of an inner side of the medium cap 300 to be mounted over the medium cap screw part 317. A hub fixing bump 319 is provided at an upper end of the medium cap screw part 317 at the inner side of the medium cap 300. A portion of the medium cap screw part 317 not used to be engaged with the hub outer wall screw part 417 is coupled to the syringe screw part 601.

As shown in FIG. 26, the hub outer wall screw part 417 is provided at the lateral surface of the hub lower body 440 to be coupled to the medium cap screw part 317. The needle fixing body 404 is provided at the center of the hub lower body 440, and the needle N is inserted into the needle fixing body 404.

A plurality of wing-type support unit fixers 412 are provided at an upper surface of the hub lower body 440 around the needle fixing body 404. Four wing-type support unit fixers 412 are shown in FIG. 26, but the present disclosure is not limited thereto.

Also, a medium cap fixing through-hole 419 may also be provided at the upper surface of the hub lower body 440, and the medium cap fixing through-hole 419 and a through-hole (not shown) of the hub fixing bump 319 may be engaged by a screw or the like.

As shown in FIG. 27, an upper end (or an upper portion) and a lower end (or a lower portion) of a small cap cylindrical wall body lower part 217 of the small cap cylindrical wall body 210 have the same radius while a small cap cylindrical wall body upper part 215 of the small cap cylindrical wall body 210 is configured to have a radius that decreases toward an upper end (or an upper portion) of the small cap cylindrical wall body upper part 215. With such a configuration, deviation of the wing-type support unit wing 108 to the outside through the small cap upper surface through-hole 203 is prevented.

In the small cap 200 of the first embodiment, a thickness (or a height) of the small cap supporting plate 206 is the same as that of the small cap supporting plate wing-shaped protrusion 211, which is the small cap supporting plate 206 at the inner side of the small cap 200 at which the wing-type support unit insertion through-hole 204 is provided or is the small cap supporting plate 206 at the outer side of the small cap 200.

Conversely, in the small cap 200 of the third embodiment, a thickness (or a height) of a small cap supporter 216 provided at the inner side of the small cap 200 is less than that of the small cap supporting plate wing-shaped protrusion 211, which is the small cap supporter 216 provided at the outer side of the small cap 200. Also, as shown in FIG. 25, the wing-type support unit insertion through-hole 204 is located to be lower than an upper surface of the small cap supporting plate wing-shaped protrusion 211.

The medium cap 300 is configured to have a long cylindrical shape. The medium cap 300 is configured such that the medium cap cylindrical wall body 310 having a cylindrical shape and the ring-shaped medium cap upper surface 301 having a circular-shaped medium cap upper surface through-hole 304 are connected to each other and installed therein, and the hub fixing bump 319 and the medium cap screw part 317 are provided inside the medium cap 300.

The hub fixing bump 319 serves as an upper end blocking plate when an upper portion of the medium cap screw part 317 is screw-coupled and engaged.

The upper portion of the medium cap screw part 317 is engaged with the hub outer wall screw part, and the remaining portions thereof are engaged with the syringe screw part 601.

A plurality of medium cap external protrusions 313, which are each configured to have a rod shape, are provided at the outer side wall of the medium cap 300. When each of the plurality of medium cap external protrusions 313 is coupled to the large cap 500, the medium cap external protrusion 313 is mounted at an inner side recess (not shown) of the large cap 500 or between inner side protrusions of the large cap 500 to be able to fix the large cap 500 over the medium cap 300.

FIG. 29a is the same as FIG. 16a, and shows a pen needle state before the pen needle 10 comes into contact with the skin of a user.

FIG. 29b is the same as FIG. 16b, the needle N protrudes outside the small cap 200 to pierce the skin when the injection medication administration push button 609 is pressed such that an injection medication is administered. At this point, as the spring 700 is contracted, the wing-type support unit fixer 412 configured to have a hook shape is coupled to the wing-type support unit recess 109 of the wing-type support unit 100 inside the hub 400.

FIG. 29c is the same as FIG. 16d. That is, when the injection medication administration push button 609 is released after the administration of the injection medication is completed, the contracted spring 700 stretches to push the small cap supporting plate 206 upward so that, as the spring 700 is restored, the small cap 200 is moved upward and the wing-type support unit 100 is located below the small cap supporting plate 206. At this point, the wing-type support unit fixer 412 having the hook shape of the hub 400 is maintained in a state of being hooked to the wing-type support unit 100 and the wing-type support unit recess 109.

While the present disclosure has been shown and described with reference to specific embodiments thereof, the present disclosure is not limited to the specific embodiments, and various changes and modification may be derived by those skilled in the art from the above description. Therefore, the spirit of the present disclosure should be understood from only the following claims and all equal or equivalent variations thereof fall within the scope of the present disclosure.

INDUSTRIAL APPLICABILITY

The pen needle provided with a safety protection system of the present disclosure is applied to a pen-type syringe configured to administer insulin for the treatment of diabetes.

What is claimed is:

1. A pen needle configured such that, when an injection medication administration push button is pressed and a needle protrudes outside a first cap through a first cap upper surface through-hole and then the injection medication administration push button is released, the needle is inserted into the first cap through the first cap upper surface through-hole to be prevented from protruding outside the first cap through the first cap upper surface through-hole, the pen needle comprising:
   a wing-type support unit provided with a needle fixing body insertion tube having a cylindrical shape, and having a plurality of wing-type support wings disposed along a rim of the needle fixing body insertion tube;
   the first cap having a ring-shaped first cap upper surface connected to and installed at a first cap cylindrical wall body, and configured to enable the wing-type support unit to be inserted into the first cap; and
   a hub provided with a needle fixing body into which the needle is inserted at a center of the hub, and configured to enable the needle fixing body to be moved according to whether the injection medication administration push button is pressed, wherein the needle fixing body is inserted into the needle fixing body insertion tube.

2. The pen needle of claim 1, further comprising:
a spring mounted around the needle fixing body.

3. The pen needle of claim 2, wherein the first cap is provided below the first cap cylindrical wall body, wherein the first cap is further provided with a first cap supporter having a wing-type support unit insertion through-hole at a center of the first cap, and
the spring is located below the first cap supporter.

4. The pen needle of claim 3, wherein a wing-type support unit blocking bump is provided at a bottom surface of the first cap supporter to block unfolding of the plurality of wing-type support wings when the wing-type support unit is moved below the first cap supporter.

5. The pen needle of claim 4, wherein a wing-type support unit recess is provided at a lower portion of the needle fixing body insertion tube, and a needle fixing body bump is provided at a lower portion of the needle fixing body.

6. The pen needle of claim 4, wherein a wing-type support unit recess is provided at a lower portion of the needle fixing body insertion tube, and a wing-type support unit fixer having a hook shape is provided at an upper surface of a hub lower body around the needle fixing body.

7. The pen needle of claim 4, wherein, when the wing-type support unit is moved below the first cap supporter, the wing-type support unit recess and the needle fixing body bump are engaged or the wing-type support unit recess and the wing-type support unit fixer are engaged.

8. The pen needle of claim 7, further comprising:
a second cap provided at an outer side of the first cap cylindrical wall body, mounted over the hub lower body, and having a ring-shaped second cap upper surface that is connected to and installed at a second cap cylindrical wall body.

9. The pen needle of claim 8, wherein the hub is further provided with a second cap fixer having a fence shape at an upper surface rim of the hub lower body.

10. The pen needle of claim 9, wherein a second cap fixing recess is provided at an outer side of the second cap fixer of the hub,
a second cap bump is provided at a lower portion of an inner side of the second cap, and
the second cap fixing recess and the second cap bump are engaged.

11. The pen needle of claim 9, wherein a second cap fixing bump is provided at an outer side of the second cap fixer of the hub,
a second cap body recess is provided at a lower portion of an inner side of the second cap, and
the second cap fixing bump and the second cap body recess are engaged.

12. A pen needle configured such that, when an injection medication administration push button is pressed and a needle protrudes outside a first cap through a first cap upper surface through-hole and then the injection medication administration push button is released, the needle is inserted into the s first cap through the first cap upper surface through-hole to be prevented from protruding outside the first cap through the first cap upper surface through-hole, the pen needle comprising:
the first cap having a ring-shaped first cap upper surface connected to and installed at a first cap cylindrical wall body;
a wing-type support unit provided with a needle fixing body insertion tube having a cylindrical shape, having a plurality of wing-type support wings disposed along a rim of the needle fixing body insertion tube, inserted inside the first cap cylindrical wall body, and moved according to whether the injection medication administration push button is pressed; and
a hub provided with a needle fixing body into which the needle is inserted at a center of the hub, wherein the needle fixing body is inserted into the needle fixing body insertion tube.

13. The pen needle of claim 12, further comprising:
a spring mounted around the needle fixing body,
wherein the first cap is provided below the first cap cylindrical wall body and is further provided with a first cap supporter having a wing-type support unit insertion through-hole at a center of the first cap, and
the spring is located below the first cap supporter.

14. The pen needle of claim 13, wherein the first cap is provided below the first cap cylindrical wall body and is further provided with the first cap supporter having the wing-type support unit insertion through-hole at the center of the first cap, and
the spring is located below the first cap supporter.

15. The pen needle of claim 14, further comprising:
a second cap provided at an outer side of the first cap cylindrical wall body, mounted at an outer side of the hub lower body, and having a ring-shaped second cap upper surface that is connected to and installed at a second cap cylindrical wall body.

16. The pen needle of claim 15, wherein a hub fixing bump is provided at an inner side of the second cap, and second cap screw part is provided below the hub fixing bump.

17. The pen needle of claim 16, wherein the hub is provided with a plurality of wing-type support unit fixers having a hook shape at an upper surface of the hub lower body around the needle fixing body, and
a screw part is provided at a lateral surface of the outer side of the hub lower body.

18. The pen needle of claim 17, wherein a plurality of second cap external protrusions having a rod shape are provided at an outer side wall of the second cap.

19. The pen needle of claim 18, wherein the first cap is configured such that a first cap cylindrical wall body upper part of the first cap cylindrical wall body is formed to have a radius that decreases toward an upper end of the first cap.

20. The pen needle of claim 19, wherein the first cap is configured such that the wing-type support unit insertion through-hole is positioned to be lower than an upper surface of a first cap supporting plate wing-shaped protrusion, which is a first cap supporter located at the outer side of the first cap cylindrical wall body.

* * * * *